US006428971B1

(12) United States Patent
Shinabarger et al.

(10) Patent No.: US 6,428,971 B1
(45) Date of Patent: *Aug. 6, 2002

(54) TEICHOIC ACID ENZYMES AND ASSAYS

(75) Inventors: Dean L. Shinabarger, Portage; Steven M. Swaney, Kalamazoo; Sara E. Morin, Richland, all of MI (US)

(73) Assignee: Pharmacia & Upjohn Company, Kalamazoo, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/851,435

(22) Filed: May 5, 1997

Related U.S. Application Data

(63) Continuation of application No. PCT/US97/07123, filed on May 5, 1997.
(60) Provisional application No. 60/016,868, filed on May 7, 1996.

(51) Int. Cl.[7] .............................. C12Q 1/48; C12N 9/10; C12N 9/12

(52) U.S. Cl. .............................. 435/15; 435/4; 435/193; 435/194

(58) Field of Search ................................. 435/193, 194, 435/195, 196, 4, 15; 514/1, 23; 558/70, 156

(56) References Cited

PUBLICATIONS

Fischer "Lipoteichoic acid and lipids in the membrane of *Staphylococcus aureus*" Med Microbiol Immunol (Berl). May 1994; 183(2): 61–76.

Boylan et al. "Regulation of the bacterial cell wall: analysis of a mutant of *Bacillus subtilis* defective in biosynthesis of teichoic acid" J Bacteriol. Apr. 1972; 110(1): 281–290.

Lambert et al. "Occurrence and function of membrane teichoic acids" Biochimica et Biophysica Acta. May 1977; 472: 1–12.

Hancock et al. "In vitro synthesis of the unit that links teichoic acid to peptidoglycan" J Bacteriol. Mar. 1976; 125(3): 880–886.

Morioka et al. "Carbohydrates in staphylococcus–aureus by means of the biotinylated wheat germ agglutinin and streptavidin–gold labeling technique II" J Electron Microscopy. Jun. 1989; 38(4) 258.

*Mol. Microbiol.*, 2, pp 735–741 (1988).

*Mol. Microbiol.*, 3, pp 1257–1268 (1989).

*Mol.Gen. Genet.*, 215, pp 388–394 (1989).

*J. Gen. Microbiol.*, 137, pp 929–941 (1991).

*J. Biol. Chem.*, 268, pp 16648–16654 (1993).

*Proc. Nat. Acad. Sci. USA*, 69, pp 2386–2390 (1972).

*J. Bacter.*, 176, pp 7252–7259 (1994).

*J. Bacter.*, 174, pp 646–649 (1992).

*Primary Examiner*—Elizabeth Slobodyansky
(74) *Attorney, Agent, or Firm*—Meuting, Raasch & Gebhardt, P.A.

(57) ABSTRACT

This invention discloses a novel substrate and assay for the TAP enzyme. In addition novel DNA, proteins and peptides from genes and proteins associated with bacterial teichoic acid biosynthetic pathways, specifically the rodC gene and proteins and variations thereof are disclosed.

54 Claims, 22 Drawing Sheets

```
    ATGATTGAAAACACTGTGATT
1   +---------+---------+
    M  I  E  N  T  V  I

AAATGTATTTTGAAAAGCTTGAAAAACAATTTAGGAAGTCTTGAATTGTTAATCTCAATT
22  +---------+---------+---------+---------+---------+---------+
    K  C  I  L  K  S  L  K  N  N  L  G  S  L  E  L  L  I  S  I

GATTCAGAACACCAATTTTTAGAGGATTACCAGTTATTTTTAAAGCTGAAAGAGAGACGT
82  +---------+---------+---------+---------+---------+---------+
    D  S  E  H  Q  F  L  E  D  Y  Q  L  F  L  K  L  K  E  R  R

TCAGGAACGGAATCTGAATTTCCGCTTCAAAACACTGGCTCATTAGAGTATAAAACTGAG
142 +---------+---------+---------+---------+---------+---------+
    S  G  T  E  S  E  F  P  L  Q  N  T  G  S  L  E  Y  K  T  E

ATAAATGCTCATGTTTTGCCTATGCCTGTTGAAATGGGACAAACATATGATTTTTATGTC
202 +---------+---------+---------+---------+---------+---------+
    I  N  A  H  V  L  P  M  P  V  E  M  G  Q  T  Y  D  F  Y  V

GAATTTCGAAAAAAATATGAAGATGCGGAGCAGGAACCACTCTTGAAGCGTCTTTCTGCT
262 +---------+---------+---------+---------+---------+---------+
    E  F  R  K  K  Y  E  D  A  E  Q  E  P  L  L  K  R  L  S  A

GAAGTAAATTCAATTGAGCGCGCCTTTCATGTCGATCAAACCACAGAACTTTTGATTTTA
322 +---------+---------+---------+---------+---------+---------+
    E  V  N  S  I  E  R  A  F  H  V  D  Q  T  T  E  L  L  I  L

CCTTATACAACTGATAAAGGCAACTTTTCTATTAAGGTGAAAAGAGAGGCCAAAATCATC
382 +---------+---------+---------+---------+---------+---------+
    P  Y  T  T  D  K  G  N  F  S  I  K  V  K  R  E  A  K  I  I

AGATTTGATCAAATCGAGATTAGCTCTGAAGAAATAAGCATAACAGGTTATGCGGGGTAC
442 +---------+---------+---------+---------+---------+---------+
    R  F  D  Q  I  E  I  S  S  E  E  I  S  I  T  G  Y  A  G  Y

CTGAGTTCCGAAAATCAATATCGGATAAAAAACTTGAACCTTATTTTAAAAAAGGGTGGA
502 +---------+---------+---------+---------+---------+---------+
    L  S  S  E  N  Q  Y  R  I  K  N  L  N  L  I  L  K  K  G  G
```

Fig. 3B

```
     GAAACACCTATTGAGGAAAAATTTCCAATCAAGCTAGAAAGAAAAACACATGGCCTGGAA
562  ---------+---------+---------+---------+---------+---------+
      E  T  P  I  E  E  K  F  P  I  K  L  E  R  K  T  H  G  L  E

AACATGAGAGCAGATGGTTTTGTTCCGGAACTGTATGATTTTGAAGTGAAAGTGCCTTTG
622  ---------+---------+---------+---------+---------+---------+
      N  M  R  A  D  G  F  V  P  E  L  Y  D  F  E  V  K  V  P  L

AAAGAAATTCCTTTCTCAAATGAAAAACGTTATGTTTATCGTCTTTTTATGGAGTATATA
682  ---------+---------+---------+---------+---------+---------+
      K  E  I  P  F  S  N  E  K  R  Y  V  Y  R  L  F  M  E  Y  I

TGCAATGACGATGAAGGAACGGATATTCAGTTCAACAGCACTGCTCTTGTTTTAGGAGAT
742  ---------+---------+---------+---------+---------+---------+
      C  N  D  D  E  G  T  D  I  Q  F  N  S  T  A  L  V  L  G  D

CGAAAAAACAAATTAAAAGGATTAGTAAGTATTATTAAAACAAACAACGCACCAGTTCGT
802  ---------+---------+---------+---------+---------+---------+
      R  K  N  K  L  K  G  L  V  S  I  I  K  T  N  N  A  P  V  R

TATGAAGTCTTTAAGAAAAAGAAAAAGCAGACTCTAGGTATCAGAGTAAACGACTATAGC
862  ---------+---------+---------+---------+---------+---------+
      Y  E  V  F  K  K  K  K  K  Q  T  L  G  I  R  V  N  D  Y  S

CTGAAAACAAGGATGAAATACTTTATTAAAGGAAAGAAGAAGAGATTAGTATCAAAAATA
922  ---------+---------+---------+---------+---------+---------+
      L  K  T  R  M  K  Y  F  I  K  G  K  K  K  R  L  V  S  K  I

AAAAAGATCACAAAAATGAGAAACAAGTTAATCACTAAAACATACAAATCTCTATTCATG
982  ---------+---------+---------+---------+---------+---------+
      K  K  I  T  K  M  R  N  K  L  I  T  K  T  Y  K  S  L  F  M

ATGGCTAGCAGAATGCCAGTTAAAAGGAAAACAGTCATTTTTGAAAGTTTTAATGGGAAA
1042 ---------+---------+---------+---------+---------+---------+
      M  A  S  R  M  P  V  K  R  K  T  V  I  F  E  S  F  N  G  K

CAATACAGTTGTAATCCGAGAGCGATTTACGAATATATGCGGGAAAACCACCCTGAGTAT
1102 ---------+---------+---------+---------+---------+---------+
      Q  Y  S  C  N  P  R  A  I  Y  E  Y  M  R  E  N  H  P  E  Y
```

Fig. 3C

```
         AAAATGTATTGGAGTGTAAATAAACAATATTCAGCGCCTTTTGATGAAAAGGGAATTCCT
1162     ---------+---------+---------+---------+---------+---------+
          K  M  Y  W  S  V  N  K  Q  Y  S  A  P  F  D  E  K  G  I  P

TACATTAATCGCCTCTCATTAAAATGGCTCTTCGCTATGGCAAGAGCTGAGTATTGGGTT
1222     ---------+---------+---------+---------+---------+---------+
          Y  I  N  R  L  S  L  K  W  L  F  A  M  A  R  A  E  Y  W  V

GTTAACAGCCGGCTTCCATTATGGATTCCGAAACCTAGTCATACAACATATTTACAAACA
1282     ---------+---------+---------+---------+---------+---------+
          V  N  S  R  L  P  L  W  I  P  K  P  S  H  T  T  Y  L  Q  T

TGGCATGGCACACCTTTAAAAAGACTTGCAATGGATATGGAAGAAGTCCATATGCCTGGT
1342     ---------+---------+---------+---------+---------+---------+
          W  H  G  T  P  L  K  R  L  A  M  D  M  E  E  V  H  M  P  G

ACAAACACCAAAAAATATAAAAGGAATTTTATCAAGGAAGCTTCTAATTGGGATTACTTG
1402     ---------+---------+---------+---------+---------+---------+
          T  N  T  K  K  Y  K  R  N  F  I  K  E  A  S  N  W  D  Y  L

ATTTCCCCAAATGGTTATTCAACTGAGATCTTTACACGGGCGTTTCAGTTTAACAAGACA
1462     ---------+---------+---------+---------+---------+---------+
          I  S  P  N  G  Y  S  T  E  I  F  T  R  A  F  Q  F  N  K  T

ATGATTGAATCTGGATATCCTAGAAATGATTTTCTTCATAATGATAATAATGAGGAAACA
1522     ---------+---------+---------+---------+---------+---------+
          M  I  E  S  G  Y  P  R  N  D  F  L  H  N  D  N  N  E  E  T

ATATCATTGATAAAGAGTAGGTTAAATATTCCTCGTGATAAAAAGGTTATTTTATATGCC
1582     ---------+---------+---------+---------+---------+---------+
          I  S  L  I  K  S  R  L  N  I  P  R  D  K  K  V  I  L  Y  A

CCTACATGGAGAGATGATCAGTTCTATGCAAAAGGGCGTTATAAGTTCGATCTCGATTTA
1642     ---------+---------+---------+---------+---------+---------+
          P  T  W  R  D  D  Q  F  Y  A  K  G  R  Y  K  F  D  L  D  L
```

Fig. 3D

```
        GATTTGCATCAACTTAGACAAGAACTTGGAAATGAATATATTGTAATCTTAAGAATGCAT
1702    ---------+---------+---------+---------+---------+---------+
        D  L  H  Q  L  R  Q  E  L  G  N  E  Y  I  V  I  L  R  M  H

T
        TATCTGGTAGCTGAGAATTTTGATTTAGGTCCTTTTGAAGGATTTGCATATGATTTTTCT
1762    ---------+---------+---------+---------+---------+---------+
        Y  L  V  A  E  N  F  D  L  G  P  F  E  G  F  A  Y  D  F  S
                  V

GCTTATGAGGATATTCGAGAATTGTATATGGTTTCTGATTTGCTGATTACTGATTATTCT
1822    ---------+---------+---------+---------+---------+---------+
        A  Y  E  D  I  R  E  L  Y  M  V  S  D  L  L  I  T  D  Y  S

TCAGTATTCTTTGATTTTGCAAATTTAAAACGGCCAATGCTATTCTTTGTCCCTGACATC
1882    ---------+---------+---------+---------+---------+---------+
        S  V  F  F  D  F  A  N  L  K  R  P  M  L  F  F  V  P  D  I

GAAACCTACCGGGACAAGTTGCGTGGTTTCTACTTTGATTTTGAAAAAGAAGCTCCTGGT
1942    ---------+---------+---------+---------+---------+---------+
        E  T  Y  R  D  K  L  R  G  F  Y  F  D  F  E  K  E  A  P  G

CCTTTGGTAAAAACTACTGAAGAAACGATTGAGGCTATCAAGCAGATCTCATCGCCTGAT
2002    ---------+---------+---------+---------+---------+---------+
        P  L  V  K  T  T  E  E  T  I  E  A  I  K  Q  I  S  S  P  D

TATAAGCTTCCGGTTTCTTTTGGTCCTTTCTATGATAAGTTTTGCTATTTAGAGTCAGGA
2064    ---------+---------+---------+---------+---------+---------+
        Y  K  L  P  V  S  F  G  P  F  Y  D  K  F  C  Y  L  E  S  G

CGTTCATCTGAAAAGGTTGTTAATACTGTATTTAAAGCTGAATAATTTAGGGGATCCAAAT
2122    ---------+---------+---------+---------+---------+---------+
        R  S  S  E  K  V  V  N  T  V  F  K  A  E  *
```

Seq.ID No.3 C1A 5'-TTCAGGATCCTTCTCTTGGAGG GTCACGGAAATAAAAG-3'

Seq.ID No.4 C2A 5'-ATTTGGATCCCCTAAATTATTCAGCTTTAAATAC-3'

```
     BamHI
       |
     TTTTGGATCCAAGGAAGAGAGTTAATGTCCTTAGTAGTTGACACTAATAAAAGGAAGCAA
  1  ---------+---------+---------+---------+---------+---------+
                                     M  S  L  V  V  D  T  N  K  R  K  Q

AAAGGAAAGAGCTTTTATACAGAGGAGCAGAAAAAAGTAATGATTGAAAACACTGTGATT
 61  ---------+---------+---------+---------+---------+---------+
      K  G  K  S  F  Y  T  E  E  Q  K  K  V  M  I  E  N  T  V  I
                    HindIII
                       |
     AAATGTATTTTGAAAAGCTTGAAAAACAATTTAGGAAGTCTTGAATTGTTAATCTCAATT
121  ---------+---------+---------+---------+---------+---------+
      K  C  I  L  K  S  L  K  N  N  L  G  S  L  E  L  L  I  S  I GATTCAGAACACCAATTTTTAGAGGATTACCAGTTATTTTTAAAGCTGAAAGAGAGACGT
181  ---------+---------+---------+---------+---------+---------+
      D  S  E  H  Q  F  L  E  D  Y  Q  L  F  L  K  L  K  E  R  R TCAGGAACGGAATCTGAATTTCCGCTTCAAAACACTGGCTCATTAGAGTATAAAACTGAG
241  ---------+---------+---------+---------+---------+---------+
      S  G  T  E  S  E  F  P  L  Q  N  T  G  S  L  E  Y  K  T  E ATAAATGCTCATGTTTTGCCTATGCCTGTTGAAATGGGACAAACATATGATTTTTATGTC
301  ---------+---------+---------+---------+---------+---------+
      I  N  A  H  V  L  P  M  P  V  E  M  G  Q  T  Y  D  F  Y  V GAATTTCGAAAAAAATATGAAGATGCGGAGCAGGAACCACTCTTGAAGCGTCTTTCTGCT
361  ---------+---------+---------+---------+---------+---------+
      E  F  R  K  K  Y  E  D  A  E  Q  E  P  L  L  K  R  L  S  A GAAGTAAATTCAATTGAGCGCGCCTTTCATGTCGATCAAACCACAGAACTTTTGATTTTA
421  ---------+---------+---------+---------+---------+---------+
      E  V  N  S  I  E  R  A  F  H  V  D  Q  T  T  E  L  L  I  L CCTTATACAACTGATAAAGGCAACTTTTCTATTAAGGTGAAAAGAGAGGCCAAAATCATC
481  ---------+---------+---------+---------+---------+---------+
      P  Y  T  T  D  K  G  N  F  S  I  K  V  K  R  E  A  K  I  I
                                                              KpnI
                                                                |
     AGATTTGATCAAATCGAGATTAGCTCTGAAGAAATAAGCATAACAGGTTATGCGGGGTAC
541  ---------+---------+---------+---------+---------+---------+
      R  F  D  Q  I  E  I  S  S  E  E  I  S  I  T  G  Y  A  G  Y CTGAGTTCCGAAAATCAATATCGGATAAAAAACTTGAACCTTATTTTAAAAAAGGGTGGA
601  ---------+---------+---------+---------+---------+---------+
      L  S  S  E  N  Q  Y  R  I  K  N  L  N  L  I  L  K  K  G  G
```

Fig. 6B

```
      GAAACACCTATTGAGGAAAAATTTCCAATCAAGCTAGAAAGAAAAACACATGGCCTGGAA
661   ---------+---------+---------+---------+---------+---------+
      E  T  P  I  E  E  K  F  P  I  K  L  E  R  K  T  H  G  L  E

AACATGAGAGCAGATGGTTTTGTTCCGGAACTGTATGATTTTGAAGTGAAAGTGCCTTTG
721   ---------+---------+---------+---------+---------+---------+
       N  M  R  A  D  G  F  V  P  E  L  Y  D  F  E  V  K  V  P  L

AAAGAAATTCCTTTCTCAAATGAAAAACGTTATGTTTATCGTCTTTTTATGGAGTATATA
781   ---------+---------+---------+---------+---------+---------+
       K  E  I  P  F  S  N  E  K  R  Y  V  Y  R  L  F  M  E  Y  I

TGCAATGACGATGAAGGAACGGATATTCAGTTCAACAGCACTGCTCTTGTTTTAGGAGAT
841   ---------+---------+---------+---------+---------+---------+
       C  N  D  D  E  G  T  D  I  Q  F  N  S  T  A  L  V  L  G  D

CGAAAAAACAAATTAAAAGGATTAGTAAGTATTATTAAAACAAACAACGCACCAGTTCGT
901   ---------+---------+---------+---------+---------+---------+
       R  K  N  K  L  K  G  L  V  S  I  I  K  T  N  N  A  P  V  R

TATGAAGTCTTTAAGAAAAAGAAAAAGCAGACTCTAGGTATCAGAGTAAACGACTATAGC
961   ---------+---------+---------+---------+---------+---------+
       Y  E  V  F  K  K  K  K  K  Q  T  L  G  I  R  V  N  D  Y  S

CTGAAAACAAGGATGAAATACTTTATTAAAGGAAAGAAGAAGAGATTAGTATCAAAAATA
1021  ---------+---------+---------+---------+---------+---------+
       L  K  T  R  M  K  Y  F  I  K  G  K  K  K  R  L  V  S  K  I

AAAAAGATCACAAAAATGAGAAACAAGTTAATCACTAAAACATACAAATCTCTATTCATG
1081  ---------+---------+---------+---------+---------+---------+
       K  K  I  T  K  M  R  N  K  L  I  T  K  T  Y  K  S  L  F  M

ATGGCTAGCAGAATGCCAGTTAAAAGGAAAACAGTCATTTTTGAAAGTTTTAATGGGAAA
1141  ---------+---------+---------+---------+---------+---------+
       M  A  S  R  M  P  V  K  R  K  T  V  I  F  E  S  F  N  G  K

CAATACAGTTGTAATCCGAGAGCGATTTACGAATATATGCGGGAAAACCACCCTGAGTAT
1201  ---------+---------+---------+---------+---------+---------+
       Q  Y  S  C  N  P  R  A  I  Y  E  Y  M  R  E  N  H  P  E  Y

EcoRI
                                                            |
      AAAATGTATTGGAGTGTAAATAAACAATATTCAGCGCCTTTTGATGAAAAGGGAATTCCT
1261  ---------+---------+---------+---------+---------+---------+
       K  M  Y  W  S  V  N  K  Q  Y  S  A  P  F  D  E  K  G  I  P

TACATTAATCGCCTCTCATTAAAATGGCTCTTCGCTATGGCAAGAGCTGAGTATTGGGTT
1321  ---------+---------+---------+---------+---------+---------+
       Y  I  N  R  L  S  L  K  W  L  F  A  M  A  R  A  E  Y  W  V
```

Fig. 6C

```
      GTTAACAGCCGGCTTCCATTATGGATTCCGAAACCTAGTCATACAACATATTTACAAACA
1381  ---------+---------+---------+---------+---------+---------+
      V  N  S  R  L  P  W  I  P  K  P  S  H  T  T  Y  L  Q  T

TGGCATGGCACACCTTTAAAAAGACTTGCAATGGATATGGAAGAAGTCCATATGCCTGGT
1441  ---------+---------+---------+---------+---------+---------+
      W  H  G  T  P  L  K  R  L  A  M  D  M  E  E  V  H  M  P  G

HindIII
                                             |
      ACAAACACCAAAAAATATAAAAGGAATTTTATCAAGGAAGCTTCTAATTGGGATTACTTG
1501  ---------+---------+---------+---------+---------+---------+
      T  N  T  K  K  Y  K  R  N  F  I  K  E  A  S  N  W  D  Y  L ATTTCCCCAAATGGTTATTCAACTGAGATCTTTACACGGGCGTTTCAGTTTAACAAGACA
1561  ---------+---------+---------+---------+---------+---------+
      I  S  P  N  G  Y  S  T  E  I  F  T  R  A  F  Q  F  N  K  T ATGATTGAATCTGGATATCCTAGAAATGATTTTCTTCATAATGATAATAATGAGGAAACA
1621  ---------+---------+---------+---------+---------+---------+
      M  I  E  S  G  Y  P  R  N  D  F  L  H  N  D  N  N  E  E  T ATATCATTGATAAAGAGTAGGTTAAATATTCCTCGTGATAAAAAGGTTATTTTATATGCC
1681  ---------+---------+---------+---------+---------+---------+
      I  S  L  I  K  S  R  L  N  I  P  R  D  K  K  V  I  L  Y  A CCTACATGGAGAGATGATCAGTTCTATGCAAAAGGGCGTTATAAGTTCGATCTCGATTTA
1741  ---------+---------+---------+---------+---------+---------+
      P  T  W  R  D  D  Q  F  Y  A  K  G  R  Y  K  F  D  L  D  L GATTTGCATCAACTTAGACAAGAACTTGGAAATGAATATATTGTAATCTTAAGAATGCAT
1801  ---------+---------+---------+---------+---------+---------+
      D  L  H  Q  L  R  Q  E  L  G  N  E  Y  I  V  I  L  R  M  H T
      TATCTGGTAGCTGAGAATTTTGATTTAGGTCCTTTTGAAGGATTTGCATATGATTTTTCT
1861  ---------+---------+---------+---------+---------+---------+
      Y  L  V  A  E  N  F  D  L  G  P  F  E  G  F  A  Y  D  F  S
               V GCTTATGAGGATATTCGAGAATTGTATATGGTTTCTGATTTGCTGATTACTGATTATTCT
1921  ---------+---------+---------+---------+---------+---------+
      A  Y  E  D  I  R  E  L  Y  M  V  S  D  L  L  I  T  D  Y  S
```

Fig. 6D

```
      TCAGTATTCTTTGATTTTGCAAATTTAAAACGGCCAATGCTATTCTTTGTCCCTGACATC
1981  ---------+---------+---------+---------+---------+---------+
      S  V  F  F  D  F  A  N  L  K  R  P  M  L  F  F  V  P  D  I

GAAACCTACCGGGACAAGTTGCGTGGTTTCTACTTTGATTTTGAAAAAGAAGCTCCTGGT
2041  ---------+---------+---------+---------+---------+---------+
      E  T  Y  R  D  K  L  R  G  F  Y  F  D  F  E  K  E  A  P  G

CCTTTGGTAAAAACTACTGAAGAAACGATTGAGGCTATCAAGCAGATCTCATCGCCTGAT
2101  ---------+---------+---------+---------+---------+---------+
      P  L  V  K  T  T  E  E  T  I  E  A  I  K  Q  I  S  S  P  D

HindIII
             |
      TATAAGCTTCCGGTTTCTTTTGGTCCTTTCTATGATAAGTTTTGCTATTTAGAGTCAGGA
2161  ---------+---------+---------+---------+---------+---------+
      Y  K  L  P  V  S  F  G  P  F  Y  D  K  F  C  Y  L  E  S  G BamHI
                                                             |
      CGTTCATCTGAAAAGGTTGTTAATACTGTATTTAAAGCTGAATAATTTAGGGGATCCAAAT
2221  ---------+---------+---------+---------+---------+---------+
      R  S  S  E  K  V  V  N  T  V  F  K  A  E  *
```

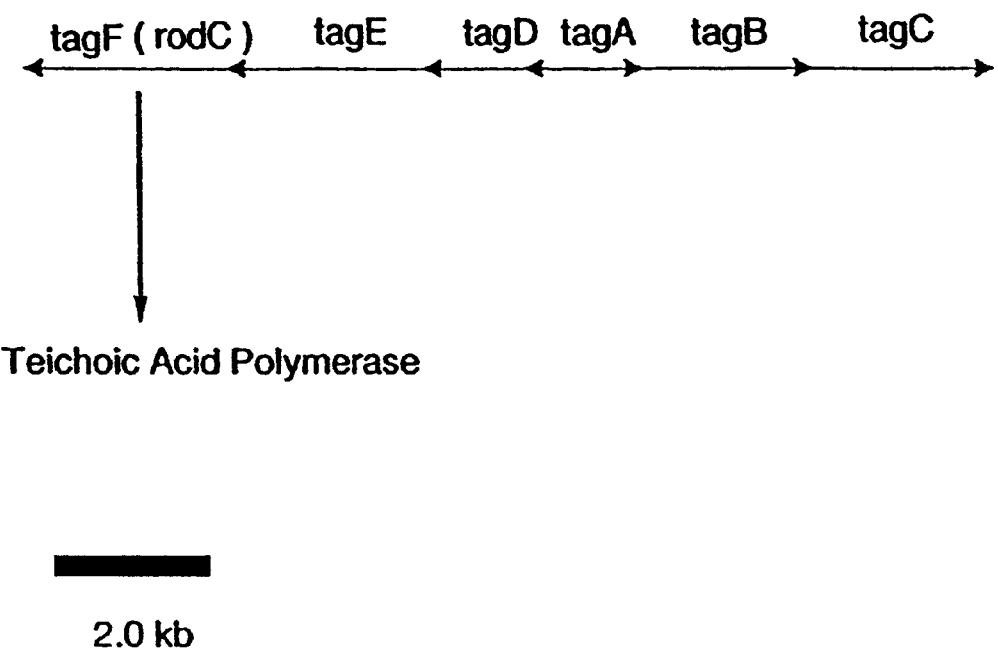
*Fig.* 10 ns

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2182 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

```
ATGATTGAAA ACACTGTGAT TAAATGTATT TTGAAAAGCT TGAAAAACAA TTTAGGAAGT      60

CTTGAATTGT TAATCTCAAT TGATTCAGAA CACCAATTTT TAGAGGATTA CCAGTTATTT     120

TTAAAGCTGA AAGAGAGACG TTCAGGAACG GAATCTGAAT TTCCGCTTCA AAACACTGGC     180

TCATTAGAGT ATAAAACTGA GATAAATGCT CATGTTTTGC CTATGCCTGT TGAAATGGGA     240

CAAACATATG ATTTTTATGT CGAATTTCGA AAAAAATATG AAGATGCGGA GCAGGAACCA     300

CTCTTGAAGC GTCTTTCTGC TGAAGTAAAT TCAATTGAGC GCGCCTTTCA TGTCGATCAA     360

ACCACAGAAC TTTTGATTTT ACCTTATACA ACTGATAAAG GCAACTTTTC TATTAAGGTG     420

AAAAGAGAGG CCAAAATCAT CAGATTTGAT CAAATCGAGA TTAGCTCTGA AGAAATAAGC     480

ATAACAGGTT ATGCGGGGTA CCTGAGTTCC GAAAATCAAT ATCGGATAAA AAACTTGAAC     540

CTTATTTTAA AAAAGGGTGG AGAAACACCT ATTGAGGAAA AATTTCCAAT CAAGCTAGAA     600

AGAAAAACAC ATGGCCTGGA AAACATGAGA GCAGATGGTT TTGTTCCGGA ACTGTATGAT     660

TTTGAAGTGA AAGTGCCTTT GAAAGAAATT CCTTTCTCAA ATGAAAAACG TTATGTTTAT     720

CGTCTTTTTA TGGAGTATAT ATGCAATGAC GATGAAGGAA CGGATATTCA GTTCAACAGC     780

ACTGCTCTTG TTTTAGGAGA TCGAAAAAAC AAATTAAAAG GATTAGTAAG TATTATTAAA     840

ACAAACAACG CACCAGTTCG TTATGAAGTC TTTAAGAAAA AGAAAAAGCA GACTCTAGGT     900
```

-continued

```
ATCAGAGTAA ACGACTATAG CCTGAAAACA AGGATGAAAT ACTTTATTAA AGGAAAGAAG    960

AAGAGATTAG TATCAAAAAT AAAAAAGATC ACAAAAATGA GAAACAAGTT AATCACTAAA   1020

ACATACAAAT CTCTATTCAT GATGGCTAGC AGAATGCCAG TTAAAAGGAA AACAGTCATT   1080

TTTGAAAGTT TTAATGGGAA ACAATACAGT TGTAATCCGA GAGCGATTTA CGAATATATG   1140

CGGGAAAACC ACCCTGAGTA TAAAATGTAT TGGAGTGTAA ATAAACAATA TTCAGCGCCT   1200

TTTGATGAAA AGGGAATTCC TTACATTAAT CGCCTCTCAT TAAAATGGCT CTTCGCTATG   1260

GCAAGAGCTG AGTATTGGGT TGTTAACAGC CGGCTTCCAT TATGGATTCC GAAACCTAGT   1320

CATACAACAT ATTTACAAAC ATGGCATGGC ACACCTTTAA AAAGACTTGC AATGGATATG   1380

GAAGAAGTCC ATATGCCTGG TACAAACACC AAAAAATATA AAAGGAATTT TATCAAGGAA   1440

GCTTCTAATT GGGATTACTT GATTTCCCCA ATGGTTATT CAACTGAGAT CTTTACACGG    1500

GCGTTTCAGT TTAACAAGAC AATGATTGAA TCTGGATATC CTAGAAATGA TTTTCTTCAT   1560

AATGATAATA ATGAGGAAAC AATATCATTG ATAAAGAGTA GGTTAAATAT TCCTCGTGAT   1620

AAAAGGTTA TTTTATATGC CCCTACATGG AGAGATGATC AGTTCTATGC AAAAGGGCGT    1680

TATAAGTTCG ATCTCGATTT AGATTTGCAT CAACTTAGAC AAGAACTTGG AAATGAATAT   1740

ATTGTAATCT TAAGAATGCA TTATCTGGTA GCTGAGAATT TTGATTTAGG TCCTTTTGAA   1800

GGATTTGCAT ATGATTTTTC TGCTTATGAG GATATTCGAG AATTGTATAT GGTTTCTGAT   1860

TTGCTGATTA CTGATTATTC TTCAGTATTC TTTGATTTTG CAAATTTAAA ACGGCCAATG   1920

CTATTCTTTG TCCCTGACAT CGAAACCTAC CGGGACAAGT TGCGTGGTTT CTACTTTGAT   1980

TTTGAAAAAG AAGCTCCTGG TCCTTTGGTA AAAACTACTG AAGAAACGAT TGAGGCTATC   2040

AAGCAGATCT CATCGCCTGA TTATAAGCTT CCGGTTTCTT TTGGTCCTTT CTATGATAAG   2100

TTTTGCTATT TAGAGTCAGG ACGTTCATCT GAAAAGGTTG TTAATACTGT ATTTAAAGCT   2160

GAATAATTTA GGGGATCCAA AT                                            2182
```

(2) INFORMATION FOR SEQ ID NO:2:

(i) SEQUENCE CHARACTERISTICS:
        (A) LENGTH: 721 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:2:

```
Met Ile Glu Asn Thr Val Ile Lys Cys Ile Leu Lys Ser Leu Lys Asn
 1               5                  10                  15

Asn Leu Gly Ser Leu Glu Leu Leu Ile Ser Ile Asp Ser Glu His Gln
                20                  25                  30

Phe Leu Glu Asp Tyr Gln Leu Phe Leu Lys Leu Lys Glu Arg Arg Ser
            35                  40                  45

Gly Thr Glu Ser Glu Phe Pro Leu Gln Asn Thr Gly Ser Leu Glu Tyr
        50                  55                  60

Lys Thr Glu Ile Asn Ala His Val Leu Pro Met Pro Val Glu Met Gly
65                  70                  75                  80

Gln Thr Tyr Asp Phe Tyr Val Glu Phe Arg Lys Lys Tyr Glu Asp Ala
```

```
                    85                  90                  95
Glu Gln Glu Pro Leu Lys Arg Leu Ser Ala Val Asn Ser Ile
            100                 105                 110
Glu Arg Ala Phe His Val Asp Gln Thr Thr Glu Leu Leu Ile Leu Pro
            115                 120                 125
Tyr Thr Thr Asp Lys Gly Asn Phe Ser Ile Lys Val Lys Arg Glu Ala
        130                 135                 140
Lys Ile Ile Arg Phe Asp Gln Ile Glu Ile Ser Ser Glu Glu Ile Ser
145                 150                 155                 160
Ile Thr Gly Tyr Ala Gly Tyr Leu Ser Ser Glu Asn Gln Tyr Arg Ile
                165                 170                 175
Lys Asn Leu Asn Leu Ile Leu Lys Lys Gly Glu Thr Pro Ile Glu
            180                 185                 190
Glu Lys Phe Pro Ile Lys Leu Glu Arg Lys Thr His Gly Leu Glu Asn
            195                 200                 205
Met Arg Ala Asp Gly Phe Val Pro Glu Leu Tyr Asp Phe Glu Val Lys
        210                 215                 220
Val Pro Leu Lys Glu Ile Pro Phe Ser Asn Glu Lys Arg Tyr Val Tyr
225                 230                 235                 240
Arg Leu Phe Met Glu Tyr Ile Cys Asn Asp Asp Glu Gly Thr Asp Ile
                245                 250                 255
Gln Phe Asn Ser Thr Ala Leu Val Leu Gly Asp Arg Lys Asn Lys Leu
            260                 265                 270
Lys Gly Leu Val Ser Ile Ile Lys Thr Asn Asn Ala Pro Val Arg Tyr
                275                 280                 285
Glu Val Phe Lys Lys Lys Lys Gln Thr Leu Gly Ile Arg Val Asn
            290                 295                 300
Asp Tyr Ser Leu Lys Thr Arg Met Lys Tyr Phe Ile Lys Gly Lys Lys
305                 310                 315                 320
Lys Arg Leu Val Ser Lys Ile Lys Lys Ile Thr Lys Met Arg Asn Lys
                325                 330                 335
Leu Ile Thr Lys Thr Tyr Lys Ser Leu Phe Met Met Ala Ser Arg Met
                340                 345                 350
Pro Val Lys Arg Lys Thr Val Ile Phe Glu Ser Phe Asn Gly Lys Gln
            355                 360                 365
Tyr Ser Cys Asn Pro Arg Ala Ile Tyr Glu Tyr Met Arg Glu Asn His
    370                 375                 380
Pro Glu Tyr Lys Met Tyr Trp Ser Val Asn Lys Gln Tyr Ser Ala Pro
385                 390                 395                 400
Phe Asp Glu Lys Gly Ile Pro Tyr Ile Asn Arg Leu Ser Leu Lys Trp
                405                 410                 415
Leu Phe Ala Met Ala Arg Ala Glu Tyr Trp Val Val Asn Ser Arg Leu
                420                 425                 430
Pro Leu Trp Ile Pro Lys Pro Ser His Thr Thr Tyr Leu Gln Thr Trp
            435                 440                 445
His Gly Thr Pro Leu Lys Arg Leu Ala Met Asp Met Glu Glu Val His
    450                 455                 460
Met Pro Gly Thr Asn Thr Lys Lys Tyr Lys Arg Asn Phe Ile Lys Glu
465                 470                 475                 480
Ala Ser Asn Trp Asp Tyr Leu Ile Ser Pro Asn Gly Tyr Ser Thr Glu
                485                 490                 495
Ile Phe Thr Arg Ala Phe Gln Phe Asn Lys Thr Met Ile Glu Ser Gly
            500                 505                 510
```

```
Tyr Pro Arg Asn Asp Phe Leu His Asn Asp Asn Glu Glu Thr Ile
        515                 520                 525
Ser Leu Ile Lys Ser Arg Leu Asn Ile Pro Arg Asp Lys Lys Val Ile
530                 535                 540
Leu Tyr Ala Pro Thr Trp Arg Asp Asp Gln Phe Tyr Ala Lys Gly Arg
545                 550                 555                 560
Tyr Lys Phe Asp Leu Asp Leu Asp Leu His Gln Leu Arg Gln Glu Leu
                565                 570                 575
Gly Asn Glu Tyr Ile Val Ile Leu Arg Met His Tyr Leu Val Ala Glu
                580                 585                 590
Asn Phe Asp Leu Gly Pro Phe Glu Gly Phe Ala Tyr Asp Phe Ser Ala
        595                 600                 605
Tyr Glu Asp Ile Arg Glu Leu Tyr Met Val Ser Asp Leu Leu Ile Thr
610                 615                 620
Asp Tyr Ser Ser Val Phe Phe Asp Phe Ala Asn Leu Lys Arg Pro Met
625                 630                 635                 640
Leu Phe Phe Val Pro Asp Ile Glu Thr Tyr Arg Asp Lys Leu Arg Gly
                645                 650                 655
Phe Tyr Phe Asp Phe Glu Lys Glu Ala Pro Gly Pro Leu Val Lys Thr
                660                 665                 670
Thr Glu Glu Thr Ile Glu Ala Ile Lys Gln Ile Ser Ser Pro Asp Tyr
        675                 680                 685
Lys Leu Pro Val Ser Phe Gly Pro Phe Tyr Asp Lys Phe Cys Tyr Leu
        690                 695                 700
Glu Ser Gly Arg Ser Ser Glu Lys Val Val Asn Thr Val Phe Lys Ala
705                 710                 715                 720
Glu
```

(2) INFORMATION FOR SEQ ID NO:3:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:3:

TTCAGGATCC TTCTCTTGGA GGGTCACGGA AATAAAAG                           38

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

ATTTGGATCC CCTAAATTAT TCAGCTTTAA ATAC                             34

(2) INFORMATION FOR SEQ ID NO:5:

(i) SEQUENCE CHARACTERISTICS:
        (A) LENGTH: 2281 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

```
TTTTGGATCC AAGGAAGAGA GTTAATGTCC TTAGTAGTTG ACACTAATAA AAGGAAGCAA      60

AAAGGAAAGA GCTTTTATAC AGAGGAGCAG AAAAAAGTAA TGATTGAAAA CACTGTGATT     120

AAATGTATTT TGAAAAGCTT GAAAAACAAT TTAGGAAGTC TTGAATTGTT AATCTCAATT     180

GATTCAGAAC ACCAATTTTT AGAGGATTAC CAGTTATTTT TAAAGCTGAA AGAGAGACGT     240

TCAGGAACGG AATCTGAATT TCCGCTTCAA AACACTGGCT CATTAGAGTA TAAAACTGAG     300

ATAAATGCTC ATGTTTTGCC TATGCCTGTT GAAATGGGAC AAACATATGA TTTTTATGTC     360

GAATTTCGAA AAAATATGA AGATGCGGAG CAGGAACCAC TCTTGAAGCG TCTTTCTGCT      420

GAAGTAAATT CAATTGAGCG CGCCTTTCAT GTCGATCAAA CCACAGAACT TTTGATTTTA     480

CCTTATACAA CTGATAAAGG CAACTTTTCT ATTAAGGTGA AAAGAGAGGC CAAAATCATC     540

AGATTTGATC AAATCGAGAT TAGCTCTGAA GAAATAAGCA TAACAGGTTA TGCGGGGTAC     600

CTGAGTTCCG AAAATCAATA TCGGATAAAA AACTTGAACC TTATTTTAAA AAAGGGTGGA     660

GAAACACCTA TTGAGGAAAA ATTTCCAATC AAGCTAGAAA GAAAAACACA TGGCCTGGAA     720

AACATGAGAG CAGATGGTTT TGTTCCGGAA CTGTATGATT TGAAGTGAA AGTGCCTTTG      780

AAAGAAATTC CTTTCTCAAA TGAAAAACGT TATGTTTATC GTCTTTTTAT GGAGTATATA     840

TGCAATGACG ATGAAGGAAC GGATATTCAG TTCAACAGCA CTGCTCTTGT TTTAGGAGAT     900

CGAAAAAACA AATTAAAAGG ATTAGTAAGT ATTATTAAAA CAAACAACGC ACCAGTTCGT     960

TATGAAGTCT TTAAGAAAAA GAAAAAGCAG ACTCTAGGTA TCAGAGTAAA CGACTATAGC    1020

CTGAAAACAA GGATGAAATA CTTTATTAAA GGAAAGAAGA AGAGATTAGT ATCAAAAATA    1080

AAAAAGATCA CAAAAATGAG AAACAAGTTA ATCACTAAAA CATACAAATC TCTATTCATG    1140

ATGGCTAGCA GAATGCCAGT TAAAAGGAAA ACAGTCATTT TTGAAAGTTT TAATGGGAAA    1200

CAATACAGTT GTAATCCGAG AGCGATTTAC GAATATATGC GGGAAAACCA CCCTGAGTAT    1260

AAAATGTATT GGAGTGTAAA TAAACAATAT TCAGCGCCTT TTGATGAAAA GGGAATTCCT    1320

TACATTAATC GCCTCTCATT AAAATGGCTC TTCGCTATGG CAAGAGCTGA GTATTGGGTT    1380

GTTAACAGCC GGCTTCCATT ATGGATTCCG AAACCTAGTC ATACAACATA TTTACAAACA    1440

TGGCATGGCA CACCTTTAAA AAGACTTGCA ATGGATATGG AAGAAGTCCA TATGCCTGGT    1500

ACAAACACCA AAAAATATAA AAGGAATTTT ATCAAGGAAG CTTCTAATTG GGATTACTTG    1560

ATTTCCCCAA ATGGTTATTC AACTGAGATC TTTACACGGG CGTTTCAGTT TAACAAGACA    1620

ATGATTGAAT CTGGATATCC TAGAAATGAT TTTCTTCATA ATGATAATAA TGAGGAAACA    1680

ATATCATTGA TAAAGAGTAG GTTAAATATT CCTCGTGATA AAAAGGTTAT TTTATATGCC    1740

CCTACATGGA GAGATGATCA GTTCTATGCA AAAGGGCGTT ATAAGTTCGA TCTCGATTTA    1800

GATTTGCATC AACTTAGACA AGAACTTGGA AATGAATATA TTGTAATCTT AAGAATGCAT    1860
```

```
TATCTGGTAG CTGAGAATTT TGATTTAGGT CCTTTTGAAG GATTTGCATA TGATTTTTCT    1920

GCTTATGAGG ATATTCGAGA ATTGTATATG GTTTCTGATT TGCTGATTAC TGATTATTCT    1980

TCAGTATTCT TTGATTTTGC AAATTTAAAA CGGCCAATGC TATTCTTTGT CCCTGACATC    2040

GAAACCTACC GGGACAAGTT GCGTGGTTTC TACTTTGATT TTGAAAAAGA AGCTCCTGGT    2100

CCTTTGGTAA AAACTACTGA AGAAACGATT GAGGCTATCA AGCAGATCTC ATCGCCTGAT    2160

TATAAGCTTC CGGTTTCTTT TGGTCCTTTC TATGATAAGT TTTGCTATTT AGAGTCAGGA    2220

CGTTCATCTG AAAAGGTTGT TAATACTGTA TTTAAAGCTG AATAATTTAG GGATCCAAA     2280

T                                                                    2281
```

(2) INFORMATION FOR SEQ ID NO:6:

(i) SEQUENCE CHARACTERISTICS:
        (A) LENGTH: 746 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (v) FRAGMENT TYPE: N-terminal (xi) SEQUENCE DESCRIPTION: SEQ ID NO:6:

```
Met Ser Leu Val Val Asp Thr Asn Lys Arg Lys Gln Lys Gly Lys Ser
1               5                   10                  15

Phe Tyr Thr Glu Glu Gln Lys Lys Val Met Ile Glu Asn Thr Val Ile
            20                  25                  30

Lys Cys Ile Leu Lys Ser Leu Lys Asn Asn Leu Gly Ser Leu Glu Leu
        35                  40                  45

Leu Ile Ser Ile Asp Ser Glu His Gln Phe Leu Glu Asp Tyr Gln Leu
    50                  55                  60

Phe Leu Lys Leu Lys Glu Arg Arg Ser Gly Thr Glu Ser Glu Phe Pro
65                  70                  75                  80

Leu Gln Asn Thr Gly Ser Leu Glu Tyr Lys Thr Glu Ile Asn Ala His
                85                  90                  95

Val Leu Pro Met Pro Val Glu Met Gly Gln Thr Tyr Asp Phe Tyr Val
            100                 105                 110

Glu Phe Arg Lys Lys Tyr Glu Asp Ala Glu Gln Glu Pro Leu Leu Lys
        115                 120                 125

Arg Leu Ser Ala Glu Val Asn Ser Ile Glu Arg Ala Phe His Val Asp
    130                 135                 140

Gln Thr Thr Glu Leu Leu Ile Leu Pro Tyr Thr Thr Asp Lys Gly Asn
145                 150                 155                 160

Phe Ser Ile Lys Val Lys Arg Glu Ala Lys Ile Ile Arg Phe Asp Gln
                165                 170                 175

Ile Glu Ile Ser Ser Glu Glu Ile Ser Ile Thr Gly Tyr Ala Gly Tyr
            180                 185                 190

Leu Ser Ser Glu Asn Gln Tyr Arg Ile Lys Asn Leu Asn Leu Ile Leu
        195                 200                 205

Lys Lys Gly Gly Glu Thr Pro Ile Glu Glu Lys Phe Pro Ile Lys Leu
    210                 215                 220

Glu Arg Lys Thr His Gly Leu Glu Asn Met Arg Ala Asp Gly Phe Val
```

```
225                 230                 235                 240

Pro Glu Leu Tyr Asp Phe Glu Val Lys Val Pro Leu Lys Glu Ile Pro
                245                 250                 255

Phe Ser Asn Glu Lys Arg Tyr Val Tyr Arg Leu Phe Met Glu Tyr Ile
                260                 265                 270

Cys Asn Asp Asp Glu Gly Thr Asp Ile Gln Phe Asn Ser Thr Ala Leu
                275                 280                 285

Val Leu Gly Asp Arg Lys Asn Lys Leu Lys Gly Leu Val Ser Ile Ile
                290                 295                 300

Lys Thr Asn Asn Ala Pro Val Arg Tyr Glu Val Phe Lys Lys Lys Lys
305                 310                 315                 320

Lys Gln Thr Leu Gly Ile Arg Val Asn Asp Tyr Ser Leu Lys Thr Arg
                325                 330                 335

Met Lys Tyr Phe Ile Lys Gly Lys Lys Arg Leu Val Ser Lys Ile
                340                 345                 350

Lys Lys Ile Thr Lys Met Arg Asn Lys Leu Ile Thr Lys Thr Tyr Lys
                355                 360                 365

Ser Leu Phe Met Met Ala Ser Arg Met Pro Val Lys Arg Lys Thr Val
                370                 375                 380

Ile Phe Glu Ser Phe Asn Gly Lys Gln Tyr Ser Cys Asn Pro Arg Ala
385                 390                 395                 400

Ile Tyr Glu Tyr Met Arg Glu Asn His Pro Glu Tyr Lys Met Tyr Trp
                405                 410                 415

Ser Val Asn Lys Gln Tyr Ser Ala Pro Phe Asp Glu Lys Gly Ile Pro
                420                 425                 430

Tyr Ile Asn Arg Leu Ser Leu Lys Trp Leu Phe Ala Met Ala Arg Ala
                435                 440                 445

Glu Tyr Trp Val Val Asn Ser Arg Leu Pro Leu Trp Ile Pro Lys Pro
                450                 455                 460

Ser His Thr Thr Tyr Leu Gln Thr Trp His Gly Thr Pro Leu Lys Arg
465                 470                 475                 480

Leu Ala Met Asp Met Glu Glu Val His Met Pro Gly Thr Asn Thr Lys
                485                 490                 495

Lys Tyr Lys Arg Asn Phe Ile Lys Glu Ala Ser Asn Trp Asp Tyr Leu
                500                 505                 510

Ile Ser Pro Asn Gly Tyr Ser Thr Glu Ile Phe Thr Arg Ala Phe Gln
                515                 520                 525

Phe Asn Lys Thr Met Ile Glu Ser Gly Tyr Pro Arg Asn Asp Phe Leu
                530                 535                 540

His Asn Asp Asn Glu Glu Thr Ile Ser Leu Ile Lys Ser Arg Leu
545                 550                 555                 560

Asn Ile Pro Arg Asp Lys Lys Val Ile Leu Tyr Ala Pro Thr Trp Arg
                565                 570                 575

Asp Asp Gln Phe Tyr Ala Lys Gly Arg Tyr Lys Phe Asp Leu Asp Leu
                580                 585                 590

Asp Leu His Gln Leu Arg Gln Leu Gly Asn Glu Tyr Ile Val Ile
                595                 600                 605

Leu Arg Met His Tyr Leu Val Ala Glu Asn Phe Asp Leu Gly Pro Phe
                610                 615                 620

Glu Gly Phe Ala Tyr Asp Phe Ser Ala Tyr Glu Asp Ile Arg Glu Leu
625                 630                 635                 640

Tyr Met Val Ser Asp Leu Leu Ile Thr Asp Tyr Ser Ser Val Phe Phe
                645                 650                 655
```

-continued

```
Asp Phe Ala Asn Leu Lys Arg Pro Met Leu Phe Phe Val Pro Asp Ile
            660                 665                 670

Glu Thr Tyr Arg Asp Lys Leu Arg Gly Phe Tyr Phe Asp Phe Glu Lys
        675                 680                 685

Glu Ala Pro Gly Pro Leu Val Lys Thr Thr Glu Glu Thr Ile Glu Ala
    690                 695             700

Ile Lys Gln Ile Ser Ser Pro Asp Tyr Lys Leu Pro Val Ser Phe Gly
705                 710                 715                 720

Pro Phe Tyr Asp Lys Phe Cys Tyr Leu Glu Ser Gly Arg Ser Ser Glu
                725             730                 735

Lys Val Val Asn Thr Val Phe Lys Ala Glu
                740             745
```

TEICHOIC ACID ENZYMES AND ASSAYS

CROSS-REFERENCE TO RELATED APPLICATIONS

This application claims the benefit of U.S. provisional application Ser. No. 60/016,868 filed May 7, 1996, under 35 USC §119(e)(i)., and a continuation of PCT/US97/07123 filed May 5, 1997.

FIELD OF THE INVENTION

This invention relates to the field of cell biology, more specifically the teichoic acid pathway. Genes and proteins related to this pathway include: Teichoic Acid Polymerase (or TAP), and CDP-Glycerol:Poly(glycerophosphate) Glycerophosphotransferase.

INFORMATION DISCLOSURE

A. L. Honeyman, G. C. Stewart, "Identification of the protein encoded by rodC, a cell division gene from *Bacillus subtilis*" *Mol. Microbiol.* (1988) 2:735–741.

A. L. Honeyman, G. C. Stewart, "The nucleotide sequence of the rodC operon of *Bacillus subtilis*. *Mol. Microbiol.* (1989) 3:1257–1268.

C. Mauel, M. Young, P. Margot, D. Karamata "The essential nature of teichoic acids in *Bacillus subtilis* as revealed by insertional mutagenesis" *Mol. Gen. Genet.* (1991) 215:388–394.

C. Mauel, M. Young, D. Karamata, "Genes concerned with synthesis of poly(glycerol phosphate), the essential teichoic acid in *Bacillus subtilis* strain 168, are organized in two divergent transcription units" *J. Gen. Microbiol.* (1991) 137:929–941.

Y. S. Park, T. D. Sweitzer, J. E. Kison, C. Kent. "Expression, purification, and characterization of CTP:Glycerol-3-phosphate cytidyltransferase from *Bacillus subtilis.*" *J. Biol. Chem.* (1993) 268:16648–16654.

BACKGROUND OF THE INVENTION

The spread of antibiotic resistance in gram positive pathogenic bacteria is a serious problem which is only beginning to be registered in the clinic. The incidence of drug resistance is increasing—especially in *Staphylococcus aureus*, *Streptococcus pneumonia,* and the enterococci. Methicillin resistant *S. aureus* (MRSA), penicillin resistant *S. pneumoniae,* and vancomycin resistant enterococci, pose a serious threat to compromised patients. Vancomycin is the only antibiotic effective against MRSA. See, C. T. Walsh, "Vancomycin resistance: decoding the molecular logic" *Science* (1993) 261:308–309; I. R. Friedland, "Therapy of penicillin- and cephalosporin-resistant pneumococcal infections" *Trends Clinic Pract.* (1993) 25:451–455 and S. Dutka-Malen, and P. Courvalin, "Update on glycopeptide resistance in enterococci" *Antimicrob News* (1990) 7:81–88.

The cell wall teichoic acid pathway is found in the majority of gram positive bacteria, and studies with *Bacillus subtilis* have revealed that it is essential to cell viability. See, C. Mauel, M. Young, P. Margot, D. Karamata, "The essential nature of teichoic acids in *Bacillus subtilis* as revealed by insertional mutagenesis" *Mol Gen Genet* (1991) 215:388–394. The essential nature of cell wall teichoic acid may be due to the covalent attachment that it forms with peptidoglycan.

Cell wall teichoic acid, like peptidoglycan, is synthesized at the outer surface of the cell membrane using a nucleotide precursor (CDPglycerol) as the building block. Teichoic acid is a polymer of polyglycerolphosphate that is covalently attached to the peptidoglycan of gram positive bacteria. The enzyme CDP-Glycerol: Poly(glycerophosphate) glycerophosphotransferase catalyzes the polymerization of glycerolphosphate monomers from CDP-glycerol into a chain of polyglycerolphosphate linked via 1,3-phosphodiester bonds. Lipoteichoic acid is a related polymer of polyglycerolphosphate which is anchored to the cell membrane but is not attached to peptidoglycan.

There is an obvious clinical need for new antimicrobial agents which inhibit novel targets. In order to screen for unique inhibitors, essential metabolic pathways of gram positive pathogens, such as the cell wall teichoic acid pathway must be identified and their respective enzymes studied, cloned and made into useful assays and screens in order to identify novel antimicrobial agents.

SUMMARY OF THE INVENTION

This invention discloses a method of measuring and assaying the activity of the TAP enzyme. This invention also demonstrates how a common commercially available material may be used as a substrate for an important biological reaction that has previously had no substrate available for evaluating this reaction. This invention teaches the researcher and clinician that lipoteichoic can be used as a substrate to elucidate the presence and even the activity of the TAP enzyme. An embodiment of this invention is the application of this teaching to create an assay that enables one to monitor the activity of the TAP enzyme.

This invention also discloses, for the first time, the sequence of an active TAP enzyme and the nucleic acid sequence of the DNA that codes for this sequence.

This invention includes: the entire DNA sequence shown in FIG. 3 and Sequence Listing I.D. no. 1, and the DNA from residues 4 to 2274, first to last restriction site, and the DNA residues 24 to 2264. The coding DNA sequence shown in FIG. 3, alternatively named, "the rodC gene." The DNA sequences corresponding to the sequence in FIG. 3 where the residue at position 1872 is thymine in place of cytosine.

A bacterial DNA sequence that is capable of hybridizing to the DNA sequence of FIG. 3, under standard stringent conditions, to about 70 or more including, 75, 80, 85, 90, 95 or greater percent homology and having the ability to catalyze the reaction of CDP-glycerol plus $H_2O$ into teichoic or lipoteichoic acid.

The DNA sequence from *Staphylococcus aureus* that codes for the protein or protein sequence fragment from *Staphylococcus aureus* having at least 70% homology to related fragments described by FIG. 3 and FIG. 4, and that yield fragments of 7.0 kb, 5 kb, and 4.2 kb after EcoRI digest, or that yield fragments of 4.5, 3.3, 2.8 kb, after HindIII digest.

In addition to the DNA sequence, this invention describes various mutants, including: A collection of randomly mutated rodC genes. A selection of one or more randomly mutated rodC genes. A collection of bacteria having randomly mutated rodC genes. A selection of one or more bacteria having a random mutation selected from the collection of bacteria. The mutated bacteria selected from a mutant form of *B. subtilis* or *S. aureus*.

Various proteins and peptide fragments from the expressed DNA are also described. The entire protein sequence shown in FIG. 3 and FIG. 4, Sequence I.D. NO. 2, the protein sequence from residues 1–746, and the protein sequence shown in FIG. 3 and FIG. 4 where valine is the amino acid at position 616 in place of alanine. Also described are the protein sequence fragment from *Staphylococcus aureus* having at least 70% homology to related fragments described by FIG. 3 and FIG. 4, that yield fragments of 7.0 kb, 5 kb, and 4.2 kb after EcoRI digest; and the protein sequence fragment from *Staphylococcus aureus* having at least 70 % homology to related fragments described by FIG. 3 and FIG. 4 that yield fragments of 4.5, 3.3, 2.8 kb, after HindIII digest. The protein disclosed in the Southern Blot shown in FIG. 2 is described as well.

In addition to the DNA and proteins disclosed herein, this invention comprises various intermediates, intermediate vectors, plasmids and transformed or mutated cell lines. This invention comprises the DNA of the sequence disclosed in FIG. 3 incorporated into a vector selected from a cloning vector, a shuttle vector or an expression vector, any of these vectors may be plasmid vectors. The cloning vector or plasmid can be selected from any widely available or commercially available plasmids. The plasmid can be any suitable pUC type or pBR type of plasmid, such as pUC18, or pUC19, or any other suitable plasmid such as pBR322. The vector may be a typical shuttle, vector The shuttle vector may be a plasmid such as, pMK4, or pYL112Δ119. An expression vector may also he used, the expression vector is a plasmid with a very strong promoter, such as the following very strong promoters: pTrc99A, pDR540, or pET-21(+). In this nomenclature pTRC99A would be the name of the plasmid. Each plasmid used for expression of proteins has a unique promoter as follows: pTRC99A (trc promoter), pDR540 (tac promoter), pET-21(+) (T7 promoter).

Examples of plasmids would be a plasmid named pRODCAP18 comprising the cloned rodC gene, placed into the cloning vector, pUC18, the plasmid named pMKRODC comprising the the cloned rodC gene, placed into the shuttle vector pMK4, the plasmid where the plasmid was created from a rodC gene excised from a pRODCAP18 plasmid, the plasmid selected from the plasmids named pBSRODC1 or pBSRODC1, comprising the rodC gene, placed into an expression vector with a strong promoter that is pTrc99A and plasmids created where the rodC gene is excised from the pMKRODC plasmid.

These plasmids may be used to create transformed bacterial cells and collections of mutant cells and plasmids may be easily created. So there are further descriptions of a bacterial cell transformed with the various disclosed plasmids and a bacterial cell that is an *E. coli* cell, and an *E. coli* cell variously transformed that is of type DH10B.

New and novel assays are also disclosed and a most important assay disclosed herein does NOT demand the newly discovered DNA and protein although in some embodiments they are required. This invention comprises: A method of measuring the activity of the TAP enzyme comprising combining CDP-glycerol plus $H_2O$ or water plus TAP enzyme plus lipoteichoic acid and measuring the amount of lipoteichoic acid formed. In one embodiment the CDP-glycerol is radioactive CDP-glycerol, in one embodiment the activity of the TAP enzyme comprises combining radioactive CDP-glycerol plus $H_2O$ plus TAP enzyme plus lipoteichoic acid plus streptavidin SPA beads and a suitable lectin such as a wheat germ agglutinin and measuring the amount of radioactive lipoteichoic acid formed as indicated by measuring the lectin bound to the SPA bead. In all these embodiments the radioactive CDP-glycerol cna be made from [$^3$H]glycerol-3-phosphate (a.k.a. [$^3$H] glycerophosphate). A preferred method of practicing any of these assays is to treat the lipoteichoic acid to remove the alanine residues before using it in the assays, that is, before combining with the other ingredients, the lipoteichoic acid is treated to remove alanine. These assays may be used to measure the activity of TAP enzyme when it is from an impure preparation or the methods may be used where the TAP enzyme is the enzyme disclosed in FIG. 3 and FIG. 4, or Sequence ID listing number 2. The assays herein may be configured into kits for ease of application.

Also disclosed is a method of using lipoteichoic acid as a substrate for the enzymatic reaction catalyzed by the TAP protein. Lipoteichoic acid, unlike teichoic acid, is commercially available and thus makes an excellent substrate. The lipoteichoic acid can serve as an acceptor of CDP[$^3$H] glycerol. The TAP protein can be obtained from crude sources or extracts, preferably the lipoteichoic acid is prepared from *B. subtilis, S. aureus,* or *E. faecalis,* or it can be the TAP protein described in FIG. 3 and FIG. 4 and Sequence Listing I.D. no. 2, or a protein having at least about 70% homology to that protein.

A diagnostic kit utilizing the TAP enzyme and CDPglycerol to detect and monitor disease caused by gram positive bacteria can be created using the information disclosed herein. Following appropriate instructions from such a kit, a portion of the biological sample which is thought to contain lipoteichoic acid could be added to TAP and CDPglycerol, incubated for an hour or so, and the transfer of glycerol-3-phosphate from CDPglycerol to lipoteichoic acid present in the sample could be detected using the precipiation assay described below under "Precipitation Assay."

BRIEF DESCRIPTION OF THE DRAWINGS

FIG. 3. The coding nucleic acid and protein sequence for the TAP protein. The DNA sequence may be referred to as the "true rodC" or tagF gene," here from *B. subtilis.* These sequences are provided in SEQ. ID. No.s 1 and 2. The DNA Sequence of the rodC gene from *B. subtilis.* Restriction sites are indicated. The translated protein sequence is also provided. This Figure also shows the mutation at position 1871, a "T for C" DNA substitution resulting in a "V for A" amino acid substitution. The DNA from this FIG. 3 is listed as Sequence Identification number 1, SEQ. ID. NO. 1, (SEQ. ID. NO. 1 is the sequence without the mutation at position 1871). The protein from this FIG. 3 is listed in FIG. 4 and is listed as SEQ. ID. NO. 2. The numbers in the left margin in the FIGURE indicate nucleic acid residues. The ATG shown is the true start codon for the actual first amino acid of the isolated TAP enzyme. In practice, an upstream ribosome binding site is also required. The actual DNA sequence that was inserted into the plasmid is shown in FIG. 6. Here this protein, sequence shown in this Figure, SEQ. ID.2, and FIG. 4, was actually expressed in *E. coli* using the plasmid pBSRODC1.

FIG. 5. The nucleic acid sequence for two primers used to clone the true rodC (tagF) gene. These sequences are provided in SEQ. ID. Nos. 3 and 4.

FIG. 6. The coding nucleic acid and protein sequence for the TAP protein, including restriction sites, mutations, binding sites and other information. These sequences are provided in SEQ. ID. No.s 1, 2, 5 & 6. The DNA Sequence of the rodC gene from B. subtilis. Restriction sites are indicated. The putative translated protein sequence is also provided. This Figures also shows the mutation at position 1871, a "T for C" DNA substitution resulting in a "V for A" amino acid substitution. The DNA from this FIG. 6 is listed as Sequence Identification number 5 (Seq. I.D. No. 5 is the sequence without the mutation at position 1871). The protein only from this FIG. 6 is listed in Sequence Chart 5 and is listed as SEQ. ID. NO. 6. The numbers in the left margin in the FIGURE indicate nucleic acid residues. The ATG at nucleic acid residue 25–27 corresponds to the methionine translation start site predicted through computer analysis by reference to Honeyman and Stewart. The ATG underlined in nucleic acid residues 100–102 corresponds to the methionine (underlined and bold M) which is the actual first amino acid of the isolated TAP enzyme. Note, the actual DNA sequence (with restriction sites noted) that was inserted into the plasmid is shown here and it includes an upstream ribosome binding site that is downstream from the putative start codon at position 25–27. The actual ribosome binding site is at position 83–87. The actual ribosome binding site is apparently AGGAG, other ribosome binding sites could be engineered such as in AGGAGA site. See SEQ. ID. NOs 1 and 2).

FIG. 7. Mutant protein sequence for the TAP enzyme. The sequence is provided in SEQ. ID. No. 6. The putative amino acids, or protein from FIG. 6, including the single amino acid mutation are shown. The amino acids from this FIG. 7 are listed separately as SEQ. ID. NO. 6 (SEQ. ID. NO. 6 is the sequence without the mutation at position 616).

FIG. 10. B. subtilis teichoic acid biosynthetic operon showing the location of the rodC (tagF) gene which codes for teichoic acid polymerase.

ADDITIONAL DESCRIPTION OF THE INVENTION

Figure 1:
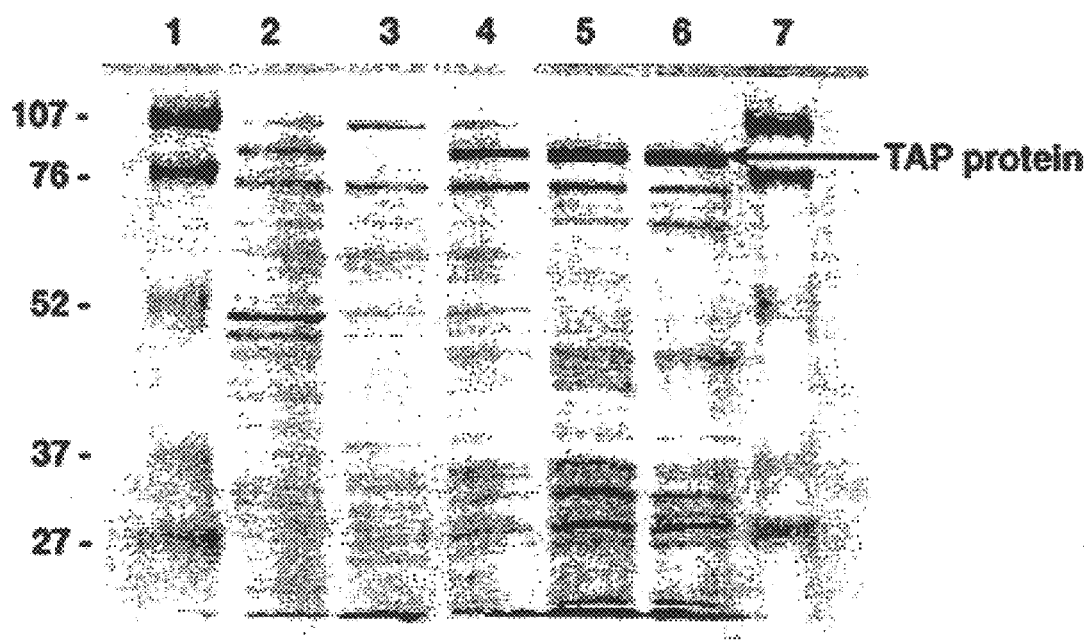
FIG. 1. SDSPAGE of TAP purification scheme. Lanes 1 and 7 are molecular weight markers; lane 2 is the soluble protein fraction from cells containing overexpressed TAP; lane 3 is the membrane from the vector pTrc99A control; lane 4 is the 2M NaCl membrane extract from cells overexpressing TAP; lane 5 is the High Q purified TAP; and lane 6 is the Superose 12 purified TAP.
Figure 2:
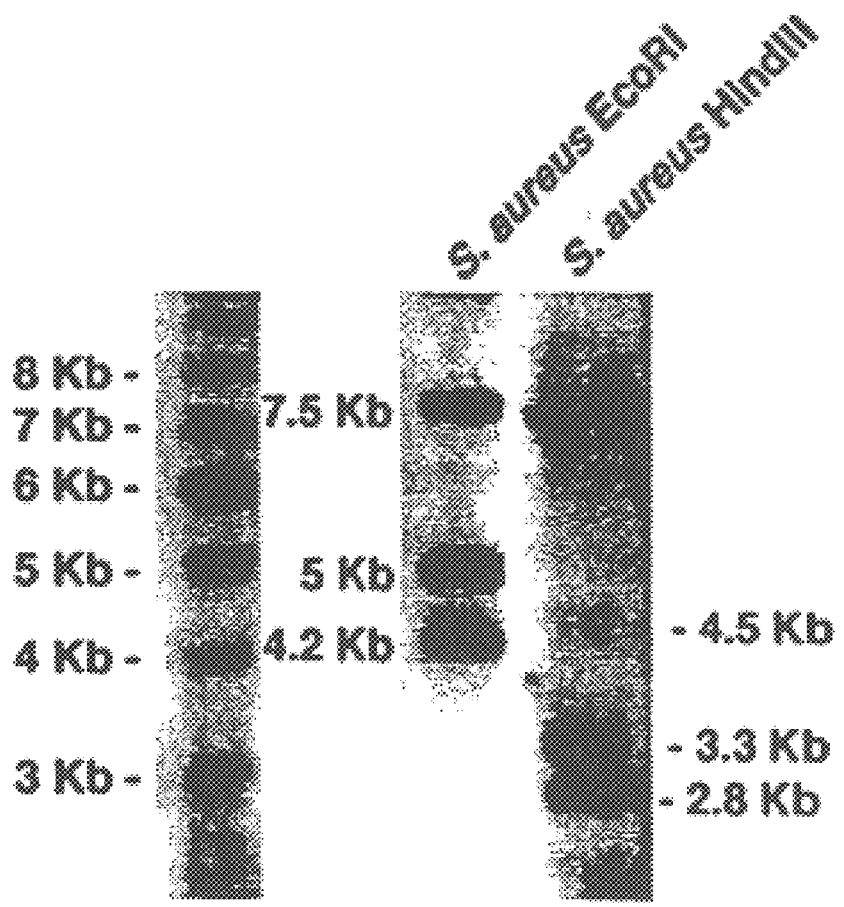
FIG. 2. Southern blot showing the DNA sequence identified as being homologous to the sequence disclosed in FIG. 3 only from the bacteria *Staphylococcus aureus.*

This invention discloses a recombinant form of Teichoic Acid Polymerase (or TAP), also known as CDP-Glycerol:Poly(glycerophosphate) Glycerophosphotransferase, its amino acid sequence and the DNA that codes for this enzyme. In addition, vectors, plasmids, probes and cells expressing this enzyme and assays incorporating the enzyme and disclosed herein, and all useful in some stage of discovery of new antibiotics, or the monitoring of disease states.

The genes responsible for cell wall teichoic acid synthesis in B. subtilis have been located in an operon on the chromosome, C. Mauel, M. Young, D. Karamata, "Genes concerned with synthesis of poly(glycerol phosphate), the essential teichoic acid in Bacillus subtilis strain 168, are organized in two divergent transcription units" J. Gen. Microbiol. (1991) 137:929–941. The tag genes, A–F, have all been sequenced, Id., but only the tagD gene protein product has been purified and characterized. Y. S. Park, T. D. Sweitzer, J. E. Kison, C. Kent. "Expression, purification, and characterization of CTP:Glycerol-3-phosphate cytidyltransferase from Bacillus subtilis." J. Biol. Chem. (1993) 268:16648–16654.

RodC or rodc, also called TagF, Tagf, tagf or tagF codes for CDP-Glycerol:Poly(glycerolphosphate) Glycerophosphotransferase, which will be referred to as Teichoic Acid Polymerase, or more frequently, TAP herein. This enzyme, TAP, catalyzes the polymerization of the polyglycerolphosphate backbone of teichoic acid by linking together the glycerolphosphate moiety of CDP-glycerol into 1,3 phosphodiester linkages. Attempts to isolate deletion mutants of rodC have been unsuccessful, see, C. Mauel, M. Young, P. Margot, D. Karamata "The essential nature of teichoic acids in Bacillus subtilis as revealed by insertional mutagenesis" Mol. Gen. Genet. (1991) 215:388–394 and A. L. Honeyman, G. C. Stewart "Identification of the protein encoded by rodC, a cell division gene from Bacillus subtilis" Mol. Microbiol. (1988) 2:735–741; however, there is one temperature sensitive mutant RODC113 available for study. This strain has a point mutation in the rodC gene which decreases enzyme activity sufficiently at 55° C. to stop growth. See, Honeyman A L, Stewart G C. "The nucleotide sequence of the rodC operon of Bacillus subtilis." Mol. Microbiol. (1989) vol. 3 pp.1257–1268.

The inability of deletion mutants of rodC to survive and the fact that TAP is essential to the viability of B. subtilis suggest the temperature sensitive rodC enzyme and mutants described herein are particularly valuable. The cloning, sequencing, and partial purification of a novel form of TAP are described below.

Cloning Theory

Previous investigators have attempted to identify and clone the rodc gene and protein. See, A. L. Honeyman, G. C. Stewart, "Identification of the protein encoded by rodC, a cell division gene from Bacillus subtilis" Mol. Microbiol. (1988) 2:735–741 and A. L. Honeyman, G. C. Stewart, "The nucleotide sequence of the rodC operon of Bacillus subtilis. Mol. Microbiol. (1989) 3:1257–1268. These previous investigations, using the bacillus known as Bacillus subtilis, did not result in the successful production of the TAP enzyme. The previous investigations disclosed a different sequence than the open reading frame of the rodC gene disclosed here. The previous investigations disclosed a different protein, one that had a very different size and one where no compositional analysis of the putative protein sequence was ever provided. The enzyme produced from the cDNA disclosed herein has never before been produced from expressed cDNA, nor has the shortened cDNA sequence disclosed here been reported as that responsible for the entire TAP protein. Previous disclosures reported a different, larger DNA sequence and a different, purely notional protein. The sequence of an active TAP enzyme has never been reported. However, the previously reported information was useful for the creation of probes, which were then used to discover and create the DNA.

In addition to creating the sequence from Bacillus subtilis, the authors herein have isolated DNA sequences from Staphylococcus aureus that arehomologous to the tagF B. subtilis residues.

Cloning and Sequencing

The B. subtilis rodC gene encoding TAP was amplified from chromosomal DNA using PCR. Sequencing revealed that Taq polymerase had performed a nucleotide misincorporation, resulting in a C to T transition at bp 1871. However, the resulting alanine to valine change in the expressed protein did not prevent the cloned gene from complementing a temperature sensitive defect in the rodC gene of B. subtilis strain RODC113.

Figures 3, 3A, 3B, 3C, 3D:
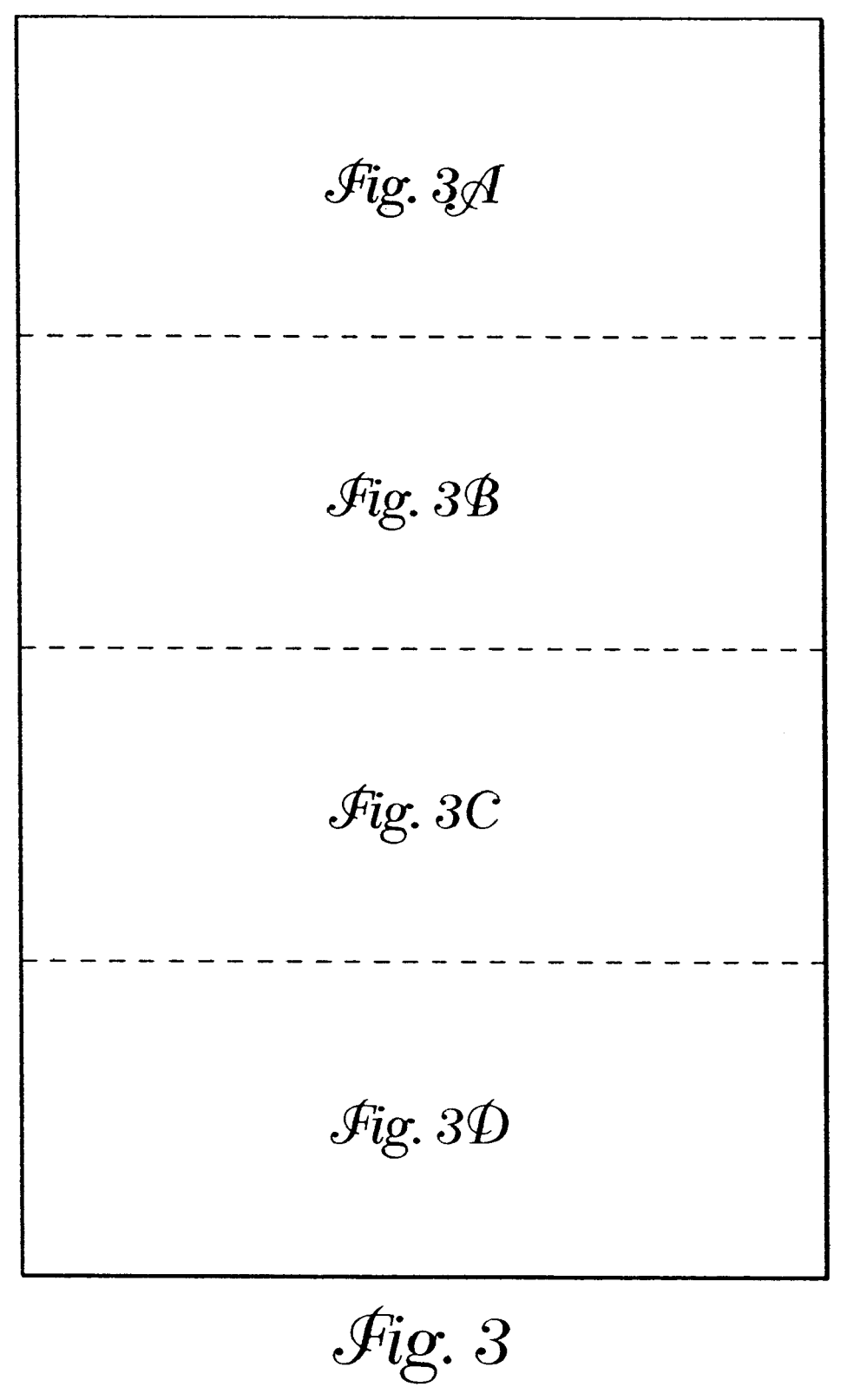

FIG. 3 shows that the DNA sequence of the PCR product cloned into pUC18 (pRODCAP18) matched the published rodC sequence exactly except for a C to T transition at bp 1871. The resulting point mutation changed an alanine in the wild-type TAP to valine. This mutant rodC gene was capable of complementing the rodC defect in the temperature sensitive B. subtilis strain RODC113 by allowing growth at the nonpermissive 55° C. temperature.

The mutant rodC gene (rodCCT) was excised from pMK-RODC as a 2.3 kb BamHI fragment and cloned into the expression vector pTrc99A to form pBSRODC1. Induction of E. coli DH10B/pBSRODC1 cells with 5 mM IPTG resulted in the appearance of a ca. 85 kd band in the cell membrane preparation (FIG. 1, lane 4). The vector control (pTrc99A) membrane preparation did not contain this band (FIG. 1, lane 3), but the 100,000×g cell extract supernatant from pBSRODC1 did show slightly less 85 kd protein than the membrane preparation (compare lanes 2 and 4, FIG. 1). N-terminal sequence analysis of the blotted protein revealed that the 85 kd polypeptide amino acid sequence began with residues 1 to 9 of SEQ ID NO:2. FIG. 3 shows that this sequence corresponds to a 2163 bp open reading frame beginning with ATG at bp 100 and ending with TAA at bp 2263.

Cloning an Homologous Sequence from *Staphylococcus aureus*

Chromosomal DNA from *S. aureus* was isolated and digested with restriction enzymes. The cut DNA was subjected to a Southern using the B. subtilis tagF gene (TAP producer) as a DNA probe. This experiment showed that S. aureus has DNA sequences that are highly homologous to the B. subtilis tagF gene.

Chromosomal DNA from S. aureus (reference=American Type Culture Collection [ATCC] 29213) was isolated and digested with the restriction enzymes EcoRI and HindIII. The DNA digests were separated by electrophoresis on a 1% agarose gel and blotted to a Nylon membrane generally following the method of Southern (Southern, E.M. 1975. "Detection of specific sequences among DNA fragments separated by gel electrophoresis," J. Mol. Biol. vol. 98, pp. 503, incorporated by reference.) A DNA probe was prepared using the method of nick translation and a 2.3 kb segment of the cloned tagF gene from B. subtilis. The S. aureus digests were hybridized to the tagF probe and several bands were identified which had homology to the cloned B. subtilis tagF gene. For example, the EcoRI digest of S. aureus chromosomal DNA yielded DNA fragments that were 7.0 kb, 5 kb, and 4.2 kb in size which hybridized well to the B. subtilis tagF gene. In addition, a HindIII digest of the same S. aureus chromosomal DNA yielded three homologous bands that migrated at 4.5 kb, 3.3 kb and 2.8 kb, respectively. As judged by visual inspection of the autoradiograms, the 4.5 kb HindIII fragment was much less homologous than either the 3.3 or 2.8 kb bands. This Southern analysis has identified tagF homologs in S.aureus that hybridize to the tagF gene of B. subtilis. These homologous S. aureus sequences represent genes coding for teichoic acid synthesis.

Production and Purification of the TAP Enzyme

TAP was overproduced under control of the trc promoter in E. coli DH10B cells. The protein was primarily located in the cell membrane, and salt extraction was used to initiate purification. TAP is associated with the membrane in B. subtilis, but the amino acid sequence does not indicate membrane spanning regions. It appears that TAP is loosely associated with the cell membrane.

Purification of TAP was hindered by the association of DNA with the enzyme preparation. Gel filtration chromatography did not improve purification, indicating that nucleic acid and protein formed a tight complex. Incubation of this preparation with Benzonase released nucleic acid fragments, but did not alter the size of the complex significantly. Future purification will require the addition of Benzonase early in purification in order to prevent the complex from forming.

Despite the nucleic acid problem, TAP was purified four-fold from the membrane preparation. The enzyme was stable for two weeks when stored in ice. Though TAP synthesizes cell wall teichoic acid in situ, lipoteichoic acid from either B. subtilis, S. aureus, or E. faecalis could serve as an acceptor of CDP[$^3$H]glycerol. The availability of a commercial source of lipoteichoic acid will allow the development of the TAP assay for a high volume screen which could lead to the discovery of TAP inhibitors. It appears that TAP recognizes the polyglycerol-phosphate backbone of either cell wall teichoic acid or lipoteichoic acid and largely ignores the proximal portion of either polymer.

Figure 8:
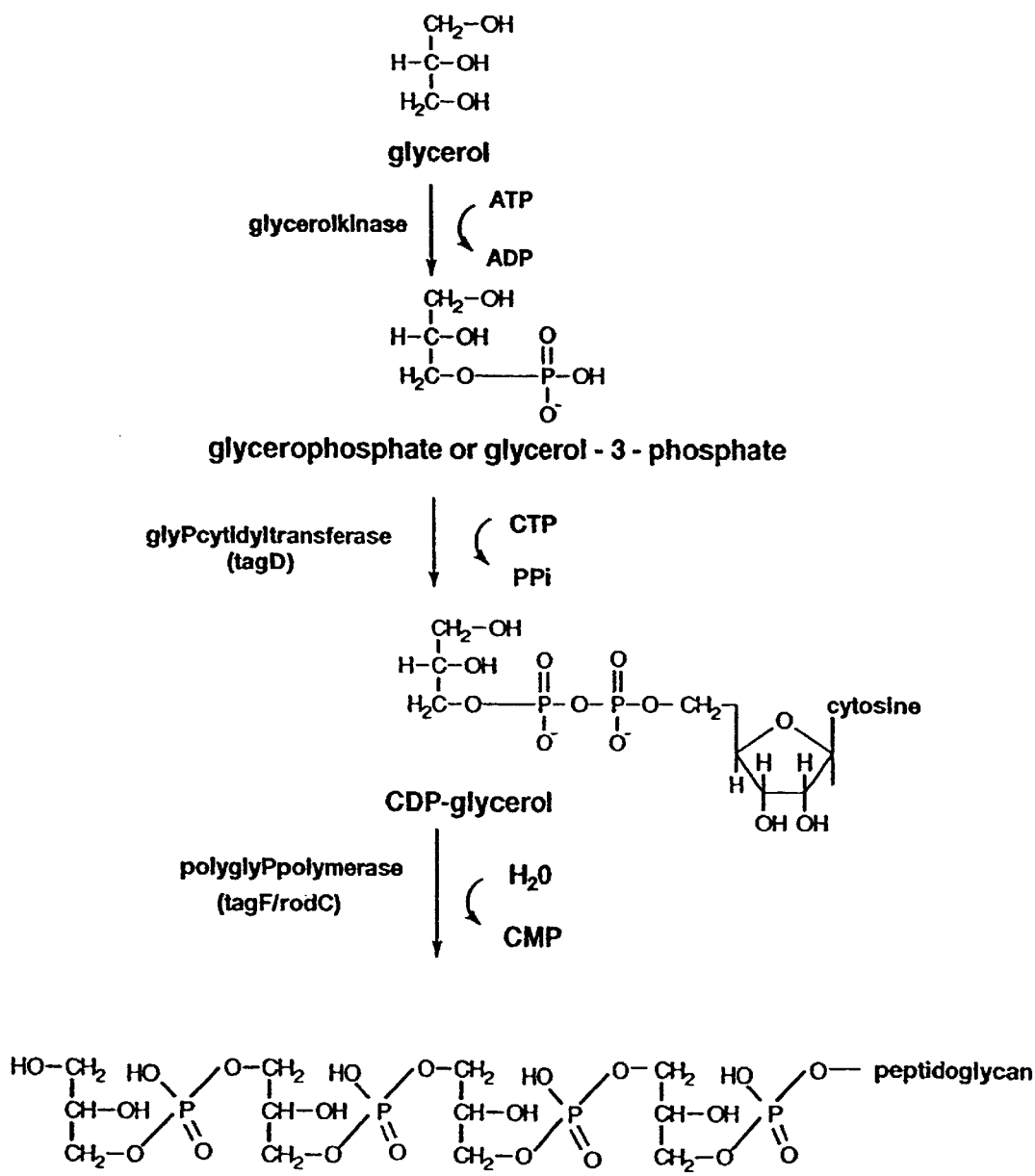
FIG. 8. The biosynthetic pathway for cell wall teichoic acid synthesis in B. subtilis. The polyglycerolphosphate polymer of teichoic acid is linked to peptidoglycan in gram positive bacteria.

The biosynthetic pathway for teichoic acid has been established for many years, yet the exact function of this anionic polymer has never been determined. One report describes the use of teichoic acid as a reserve phosphate source in which gram positive bacteria draw upon the glycerolphosphate when phosphate levels in the environment are low (Grant W D. "Cell wall teichoic acid as a reserve phosphate source in *Bacillus subtilis*" *J Bacteriol* (1979) vol. 137, pp. 35–43, incorporated by reference). While this role for teichoic acid cannot be disputed, the fact that B. subtilis cannot survive in the absence of teichoic acid synthesis under conditions of high phosphate levels (Mauel C, Young M, Margot P, Karamata D. "The essential nature of teichoic acids in *Bacillus subtilis* as revealed by insertional mutagenesis" *Mol Gen Genet* (1991) vol. 215, pp. 388–394, incorporated by reference) indicate that a more essential role is likely. Some reports point to the ability of teichoic acid to chelate divalent cations (Fischer, W. "Lipoteichoic acid and lipids in the membrane of *Staphylococcus aureus*" *Med. Microbiol. Immunol.* (1994) vol.183, pp. 61–76, incorporated by reference), but lipoteichoic acid would presumably chelate in the absence of cell wall teichoic acid. It is far more likely that the essential nature of teichoic acid is in maintaining the structural integrity of the cell wall, due to the covalent attachment to peptidoglycan (FIG. 8). Given the information disclosed herein it would be obvious to one skilled in the art to randomly mutate the cloned rodC gene, integrate the mutated gene back into the chromosome, and produce a pool of TAP mutants which can be used to study the effects of teichoic acid on gram positive cell wall integrity.

Partial Purification of TAP

The enzymatic activity of TAP was assayed using CDP [$^3$H]glycerol as the glycerolphosphate donor and B. subtilis lipoteichoic acid as the acceptor. If active, the recombinant TAP enzyme should lengthen lipoteichoic acid with radioactive glycerolphosphate monomers, producing acid precipitable radioactivity. Preliminary experiments demonstrated that the overexpressed TAP was active, therefore a purification method was initiated. Extraction of TAP from the *E. coli* membrane with 2 M NaCl produced an active TAP preparation that could be separated from the cell membrane by ultracentrifugation. Dialysis of the TAP membrane extract against Buffer A (see Material and Methods) produced the protein pattern shown in FIG. 1, lane 4.

Ten mg of the dialyzed membrane extract was placed in an ion-exhange column. Equilibration of the column with Buffer A containing 50 mM NaCl resulted in a small amount of TAP activity passing through the column in fractions 2–4, but the majority of activity eluted at the end of the 0.05 M to 0.5 M NaCl gradient. Table 1 shows that High Q chromatography resulted in a four-fold purification of TAP, and SDSPAGE analysis of these pooled fractions demonstrated that TAP was enriched (FIG. 1, lane 4). Gel filtration chromatography on Superose 12 did not increase the specific activity of the enzyme (data not shown) and this result is supported by the lack of purification evident in lane 5 of FIG. 1. TAP eluted with the void volume (mol. wt.>200 kd ) in the Superose 12 column, while it migrated as a ca. 400–600 kd protein using a TSK-400 gel filtration column. A spectrophotometric wavelength scan revealed that the sample contained a high amount of nucleic acid which presumably forms a high molecular weight complex with the proteins in the sample, including TAP.

Applications and Uses of the TAP Enzyme, Lipoteichoic Acid as a Substrate, and the Expressed Cloned cDNA Sequence Enzymatic Synthesis of Polyglycerolphosphate (Teichoic Acid) by TAP and alternative substrates for the TAP enzyme.

Figure 9:
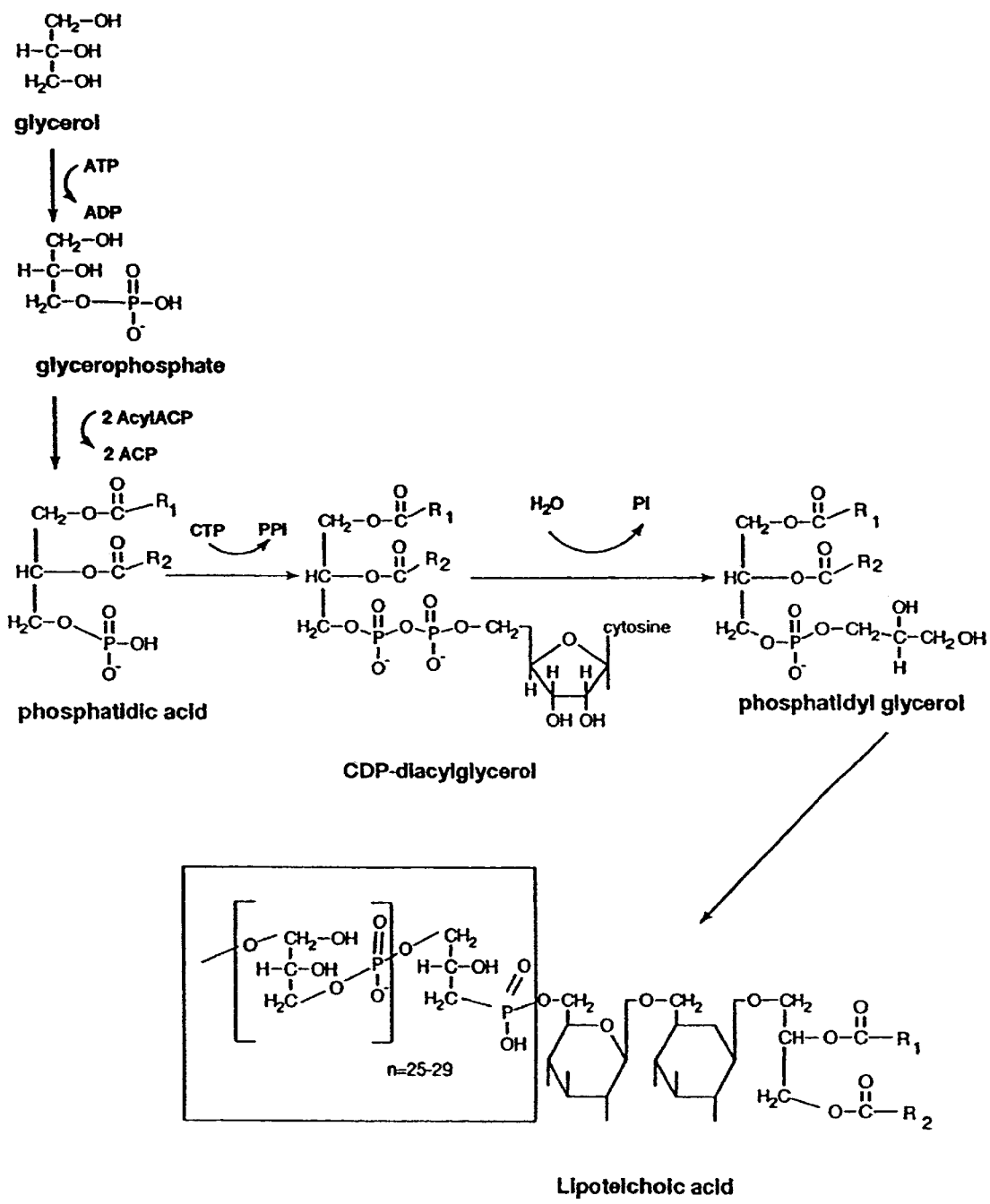
FIG. 9. The biosynthetic pathway for lipoteichoic acid synthesis in cell membrane. The fatty acyl chains of lipoteichoic acid are embedded in the cell membrane and the polyglycerolphosphate backbone is oriented out towards the cell surface.

TAP catalyzes the synthesis of the polyglycerolphosphate backbone of cell wall teichoic acid in *B. subtilis,* and this polymer is covalently attached to peptidoglycan (FIG. 8). Lipoteichoic acid is a structurally related polymer that is anchored to the cell membrane of gram positive bacteria by the fatty acyl side chains of a phospholipid moiety (FIG. 9). Both lipoteichoic acid and cell wall teichoic acid share the same polyglycerolphosphate backbone but there is evidence that TAP does not synthesize lipoteichoic acid in situ (Fischer, W. "Lipoteichoic acid and lipids in the membrane of *Staphylococcus aureus*" *Med. Microbiol. Immunol.* (1994) vol. 183, pp. 61–76). Herein, we present data that shows that lipoteichoic acid can serve as an alternate substrate for TAP. This is an important discovery, both because lipoteichoic acid is available commercially and cell wall teichoic acid is not, and because tests have suggested that soluble teichoic acid does not serve as a suitable substrate for TAP. This discovery now makes it possible to develop mechanistic screens for TAP inhibitors.

Assay Conditions

Several assays may be constructed using the TAP enzyme. Precipitation and SPA are two examples. Modification (alanine removal) of lipoteichoic acid resulted in improved activity of the recombinant TAP enzyme. Alanine ester was removed from lipoteichoic acid by resuspending 1 mg. in 0. 1M Tris-HCL buffer (pH 8.0) for 24 hr. at 37° C. Free alanine was removed by dialysis in 3500 dalton cutoff membrane agains deionized water (Fischer, W., H. U. Koch, P. Rosel, and F. Fiedler "Alanine ester-containing native lipoteichoic acids do not act as lipoteichoic acid carrier" *J. Biol. Chem.,* (1980) vol. 255, pp. 4557–4562, incorporated by reference.

Precipitation Assay

The method of Burger and Glaser was generally followed. Burger M M, Glaser L. "The synthesis of teichoic acids" *J. Biol. Chem.* (1964) vol. 239, pp. 3168–3177, incorporated by reference. A typical assay contained 1–100 µl of enzyme, 10 µl of lipoteichoic acid (1 mg/ml *B. subtilis* lipoteichoic acid [Sigma] in water), 25 µl of CDP[$^3$H]glycerol (10 mM CDPglycerol Specific Activity 8.8 µCi/µMole), and enough Buffer A to bring the total volume to 250 µl. The reaction was incubated at 37° C. for one hour, mixed with 80 µl of 3N perchloric acid, and placed on ice for 5 min. The acid treated sample was spotted on a GF/C filter and washed with 4×5 ml of 0.15 N perchloric acid before liquid scintillation counting. Control reactions lacking either lipoteichoic acid or CDP[$^3$H]glycerol were included as negative controls.

Preliminary experiments demonstrated that incubation of lipoteichoic acid and CDP[$^3$H]glycerol with TAP resulted in the formation of an acid precipitable material. When this material was analyzed by cellulose thin-layer chromatography, it remained at the origin, indicating that a high molecular weight compound had been formed in the TAP assay. Hydrolysis of this product at 100° C. in the presence of 1 N HCl resulted in the formation of degradation products which comigrated with glycerol and glycerol-3-phosphate. The chromatography profile matches that which has been reported for the acid catalyzed degradation of polyglycerol-phosphate (Burger M M, Glaser L. "The synthesis of Teichoic Acids" *J. Biol. Chem.* (1964), vol. 239, pp. 3168–3177, incorporated by reference) the data demonstrate that lipoteihoic acid can serve as an acceptor for the transfer of [$^3$H]glycerol-3-phosphate from CDP[$^3$H]glycerol in the TAP catalyzed reaction thereby lengthening the polyglycerol-phosphate chain. Table 2 shows that commercial lipoteichoic acid preparations from *S. aureus* and *S. faecalis* can also serve as acceptors for the transfer of [$^3$H]glycerol-3-phosphate from CDP[$^3$H]glycerol.

Scintillation Proximity Assay (or SPA)

This assay is based on the ability of lectins such as wheat germ agglutinin (WGA) and concanavalin A (conA) to bind the sugar moieties present on lipoteichoic acids isolated from a variety of gram positive bacteria. For example, the enzyme can be mixed with buffer, [$^3$H]CDP-glycerol, and 10 µg of *Enterococcus faecalis* lipoteichoic acid as described for the precipitation assay above. After incubating at 37° C. for 1 hour, streptavidin SPA beads (Amersham) containing biotinylated concanavilin A are added to the assay and the entire mix is incubated at room temperature for 30 min. in a 96 well plate. The conA::SPA bead conjugate will bind the radioactive lipoteichoic acid formed in the assay and the activity of the enzyme can be quantitated using a counter such as a Packard Top Counter. A variety of lipoteichoic acids can serve as substrates and the appropriate lectin can be bound to a SPA bead. For example, the glucose moieties present on the lipoteichoic acids of *Enterococcus faecalis, Enterococcus faecium,* and *Enterococcus hirae* can be bound to SPA beads containing conA. The cell wall teichoic and lipoteichoic acids of *Staphylococcus aureus* containing N-acetylglucosamine residues can be bound to WGA beads.

Alternative uses for the discovery that lipoteichoic acid can be used as a substrate for the TAP enzyme.

The discovery that lipoteichoic acid can be used as a substrate for the TAP enzyme suggests other practical applications. One obvious application of this discovery will be the creation of kits and diagnostic devises useful for the monitoring and management of disease states caused or influenced by gram positive bacteria.

Since lipoteichoic acid serves as a substrate. for TAP, in that TAP will extend the lipoteichoic acid chain by adding glycerol-3-phosphate residues from CDPglycerol, TAP could therefore be used to detect the presence of lipoteichoic acid in biological samples including blood and other bodily fluids. For example, a portion of the biological sample which is thought to contain lipoteichoic acid could be added to TAP and CDPglycerol, incubated for an hour or so, and the transfer of glycerol-3-phosphate from CDPglycerol to lipoteichoic acid present in the sample could be detected using the precipiation assay described under "Precipitation Assay."

Potential uses of TAP could therefore include the diagnosis of bacterial infection in which bacteria release lipoteichoic acid into body fluids. TAP can be used to detect lipoteichoic acid in body fluids. Antibodies which target lipoteichoic acid are currently used for lipoteichoic acid detection in clinical samples, but the discovery disclosed here makes it possible for the TAP enzyme to be used to perform the same function.

Materials and Methods

One skilled in the art should be able to reproduce and practice this invention with the information provided above, the materials and methods below are provided to further illuminate the invention and should not be considered limiting in any way.

Cloning rodC from *B. subtilis*

The published sequence of rodC was utilized to clone the gene from the *B. subtilis* chromosome using PCR, according to the following:. The primers:

C1A (5'-TTCAGGATCCTTCTCTTGGAGG GTCACGGAAATAAAAG-3'), SEQ. ID NO. 3 and

C2A (5'-ATTTGGATCCCCTAAATTATTCAGCTTTAA ATAC-3') SEQ. ID NO.4 hybridized to sequences −35 to −8 bases upstream of the putative translational start site and −15 to +9 from the stop site, respectively. Primer sequences are reproduced in Sequence Chart 3 and sequence identification numbers 3 and 4. Amplification using a program of 94° C. for 45 sec/48° C. for 45 sec/ and 72° C. for 2 min (30 cycles) resulted in the production of a 2.3 kb product which yielded EcoRI fragments of 1.5 and 0.8 kb, characteristic of rodC. The BamHI sites engineered into the primers C1A and C2A allowed for the cloning of rodC into pUC18, yielding pRODCAP18. Any other commonly available cloning vector could be used in place of pUC, including such vectors as pUC's, pUC18, pUC19, pBR322, and many other commonly available plasmids.

Complementation of the *B. subtilis* rodC mutant RODC113

The rodC gene from pRODCAP18 was excised as a 2.3 kb BamHI fragment and ligated into the BamHI site of the *E. coli*/gram positive shuttle vector pMK4 to produce pMK-RODC. The pMK4 plasmid was selected because it reproduces in both gram negative bacteria like *E. coli* and it reproduces in gram positive bacteria like *B. subtilis*. Any shuttle vector of this type should be suitable. pMKRODC was electroporated into the temperature sensitive *B. subtilis* rodC mutant RODC113 using an standard methods. The cells were plated on LB/chloramphenicol and incubated at 55° C.

Sequencing

The rodC gene present in pRODCAP18 was sequenced using deltaTaq cycle sequencing (Amersham®) and [$^{35}$S] dATP direct incorporation.

Overexpression of TAP

In order to achieve overexpression of TAP, the rodC gene was excised from pMKRODC as a 2.3 kb BamHI fragment and ligated into the BamHI site of the expression vector pTrc99A (Pharmacia) to form pBSRODC1. The expression vector pTrc99A was chosen here but any plasmid with a very strong promoter, such as pTrc99A, pDR540, or pET-21(+) should make a suitable expression plasmid. A second isolate containing rodC in the opposite orientation was designated pBSRODC2. In these examples pTRC99A would be the name of the plasmid. Each plasmid used for expression of proteins has a unique promoter as follows: pTRC99A (trc promoter), pDR540 (tac promoter), pET-21(+) (T7 promoter).

Overexpression and Partial Purification of TAP from *Escherichia coli*

A. Cell Growth and Lysis

DH10B (*E. coli*) cells transformed with pBSRODC1 were grown in 2 liters of 2× LB for 3 hr, induced with IPTG (5 mM) for 4 hr, harvested via centrifugation, and stored at −70° C. The cell pellet was resuspended in 5 ml of Buffer A (50 mM Tris-HCl, 10 mM $MgCl_2$, 1 mM DTT, 1 mM EDTA, pH 7.5) and lysed by two passages through a French Pressure Cell at 10,000 psi. Note, 2× LB can be restated as double strength Lennox Broth. IPTG stands for isopropylthio-beta-D-galactoside.

B. Extraction of TAP from the Cell Membrane

The cell lysate was centrifuged at 5,000×g for 15 min to remove unbroken cells, and the supernatant was centrifuged at 100,000×g for one hour. The resulting membrane pellet was resuspended in 25 ml of Buffer A containing 2M NaCl and extracted for two hours on a rotary shaker at 4° C. The sample was then centrifuged at 100,000×g for one hour to pellet the membrane, and the supernatant was dialyzed overnight against four liters of Buffer B (Buffer A containing 50 mM NaCl).

C. High Q Anion Exchange Chromatography

A 5 ml High Q column (BioRad®) was equilibrated with Buffer B using an Econosystem Automated Chromatography Unit (BioRad®). A portion of the 2M NaCl extract of the cell membrane representing 10 mg of total protein was applied to the column and unbound proteins were washed out with the same buffer. TAP was eluted from the column using a 0.05 to 0.5 M NaCl gradient and fractions containing TAP activity were pooled and concentrated using a Centriprep 30 ultrafiltration unit (Amicon®). The concentrated protein was dialyzed overnight against two liters of Buffer A.

TAP Enzyme Assay

The method of Burger and Glaser was generally followed. Burger M M, Glaser L. "The synthesis of teichoic acids" *J Biol Chem* (1964) vol. 239, pp. 3168–3177, incorporated by reference. A typical assay contained 1–100 μl of enzyme, 10 μl of lipoteichoic acid (1 mg/ml *B. subtilis* lipoteichoic acid [Sigma] in water), 25 μl of CDP[$^3$H]glycerol (10 mM CDPglycerol Specific Activity 8.8 μCi/μMole), and enough Buffer A to bring the total volume to 250 μl. The reaction was incubated at 37° C. for one hour, mixed with 80 μl of 3N perchloric acid, and placed on ice for 5 min. The acid treated sample was spotted on a GF/C filter and washed with 4×5 ml of 0.15 N perchloric acid before liquid scintillation counting. Control reactions lacking either lipoteichoic acid or CDP[$^3$H]glycerol were included as negative controls.

Identification of the TAP Product as Polyglycerolphosphate

The TAP assay was performed as described above in a total volume of 1 ml by scaling up the appropriate reagents. After one hour at 37° C., the product of the reaction was precipitated with 3N perchloric acid and centrifuged at 14,000×g for 15 min. The pellet was washed two times with 0.5 ml of 0.15 N perchloric acid and dried in a speed vac before resuspending in 0.1 ml of 0.3 M NH$_4$OH. At this point the soluble material represented 5.3×10$^6$ cpm per ml. Approximately 0.09 ml of this material was dried in the speed vac and subsequently resuspended in 0.1 ml of 1N HCl. This material was refluxed in a sealed vial at 100° C. and samples were removed after 16 hr of hydrolysis for analysis by thin layer chromatography using cellulose plates and the following solvent systems: Ethanol—NH$_4$acetate, pH 7.5 (7.5:3) and n-propanol—ammonia—water (6:3:1). After developing the plates in the solvent, they were dried at room temperature and cut into 1×2 cm sections for liquid scintillation counting.

Additional Disclosed Embodiments of the Invention

With this disclosure of the TAP sequence, random mutation of the cloned rodC gene may be constructed and integrated back into the chromosome thus producing a pool of TAP mutants which can be used to study the effect of teichoic acid on gram positive cell wall integrity.

Definitions

Words in this document should be given the meaning that one skilled in the art with give those words. Some examples of this follow.

BioRad® is the name of a biochemical supply company located in Hercules, Calif.

Amicon® is the name of a biochemical supply company located in Beverly, Mass.

h or hr is hour homology and homologous sequences and residues are referred to in this document. In general, these terms have meanings generally accepted by one skilled in the art. The following definitions are also provided and should control and explain any scientific disagreement concerning the meaning of the terms. Here are two definitions of homology, one in reference to DNA, or nucleic acid sequences and one in reference. to peptide or protein sequences. Nucleic acid homology definition: a nucleic acid sequence from one organism is X % homologous to that of a second organism when a gene from the second organism contains, at any point within the sequence, X nucleotide residues out of 100 which were identical to that of a similar gene of the first organism. For example, a nucleic acid sequence from *S. aureus* which is 70% homologous to that of the *B. subtilus* rodC gene would contain at any point within the sequence, 7 nucleotide residues out of 10 which were identical to that of the *B. subtilis* rodC gene.

Peptide or protein homology: a peptide or protein, which is X % homologous to that of another peptide or protein, would contain, at any point within its amino acid sequence, X amino acid residues out of 100 which were either identical or similar to that of the first amino acid sequence. For example, a peptide or protein which is 70% homologous to that of the *B. subtilis* TAP enzyme, would contain, at any point within its amino acid sequence, 7 amino acid residues out of 10 which were either identical or similar to that of the *B. subtilis* amino acid sequence. A similar amino acid is one that is of similar size, charge or hydrophilic property.

IPTG stands for isopropylthio-beta-D-galactoside. m. or min. is minute

Cloning vectors are vectors such as pUC's pUC18, pUC19, pBR322, and many other commonly available plasmids.

A cloning vector may be a shuttle vector.

A shuttle vector is a plasmid that replicates in either gram negative or gram positive bacteria. Example shuttle vectors are pMK4, and pYL112Δ119.

An expression vector is a plasmid with a very strong promoter, such as pTrc99A, pDR540, or pET-21(+).

TABLE 1

TAP Enzymatic Activity in Purification Procedure.

| Purification Step | Specific Activity nmoles/hr/mg protein |
|---|---|
| Membrane | 4.7 |
| 2M NaCl Extract of Membrane | 10.3 |
| High Q Chromatography | 39.9 |

TABLE 2

Effect of Lipoteichoic Acid Source on TAP Activity.

| Source of Lipoteichoic Acid | cpm of [$^3$H] glycerol Incorporated |
|---|---|
| *Bacillus subtilis* | 155,930 |
| *Streptococcus faecalis* | 93,814 |
| *Staphylococcus aureus* | 15,632 |

FIG. 8

Teichoic Acid Pathway in *B. subtilis*. Biosynthetic pathway for cell wall teichoic acid synthesis in *B. subtilis*. The polyglycerolphosphate polymer of teichoic acid is linked to peptidoglycan in gram positive bacteria.

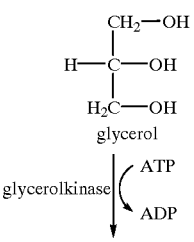

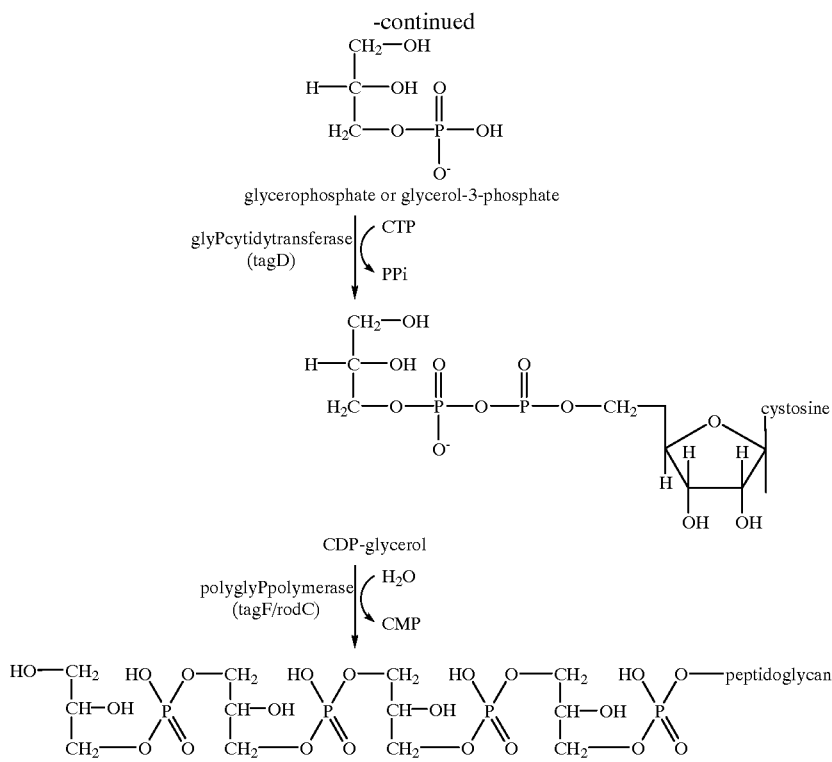
FIG. 9
Biosynthesis of Lipoteichoic Acid in *Staphylococcus aureus*. Biosynthetic pathway for lipoteichoic acid synthesis. The fatty acyl chains of lipoteichoic acid are embedded in the cell membrane and the polyglycerolphosphate backbone is oriented out towards the cell surface.
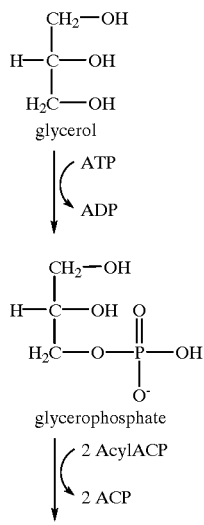

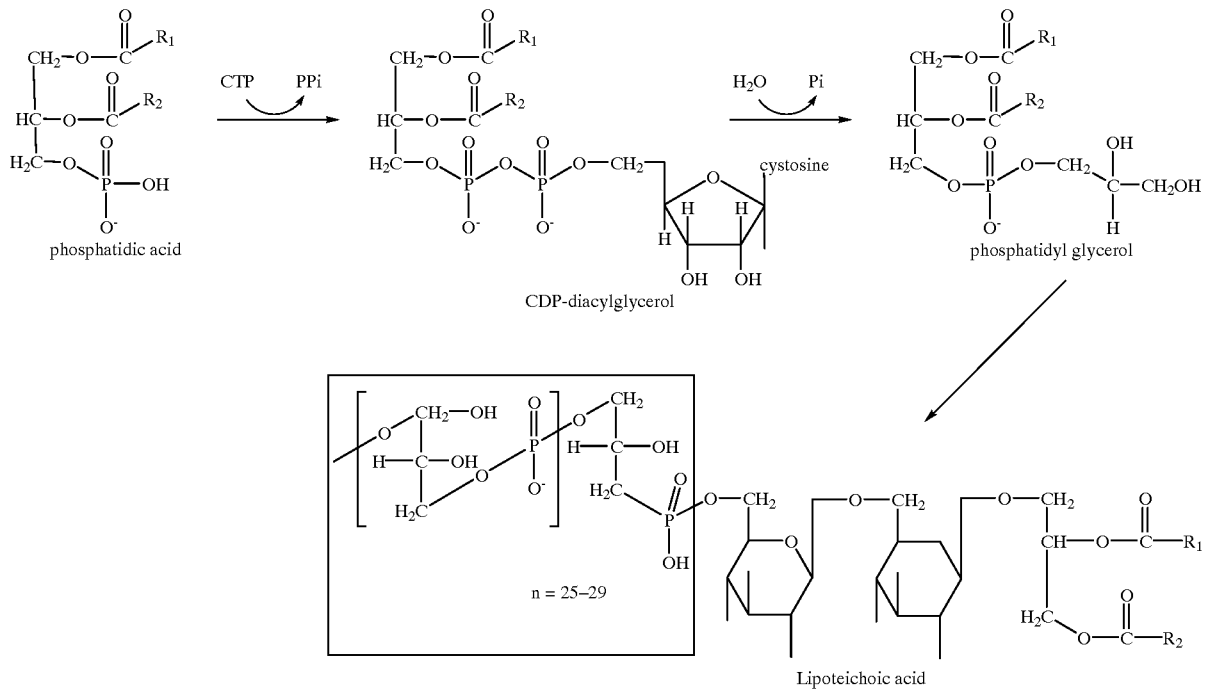

FIG. 10

B. subtilis teichoic acid biosynthetic operon showing the location of the rodC (tagF) gene which codes for teichoic acid polymerase.

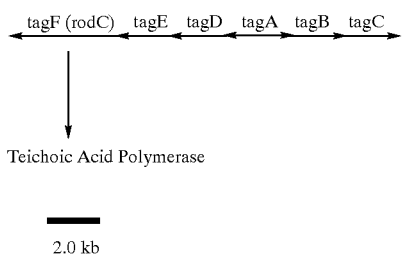

FIG. 3

Figures 6, 6A, 6B, 6C, 6D:
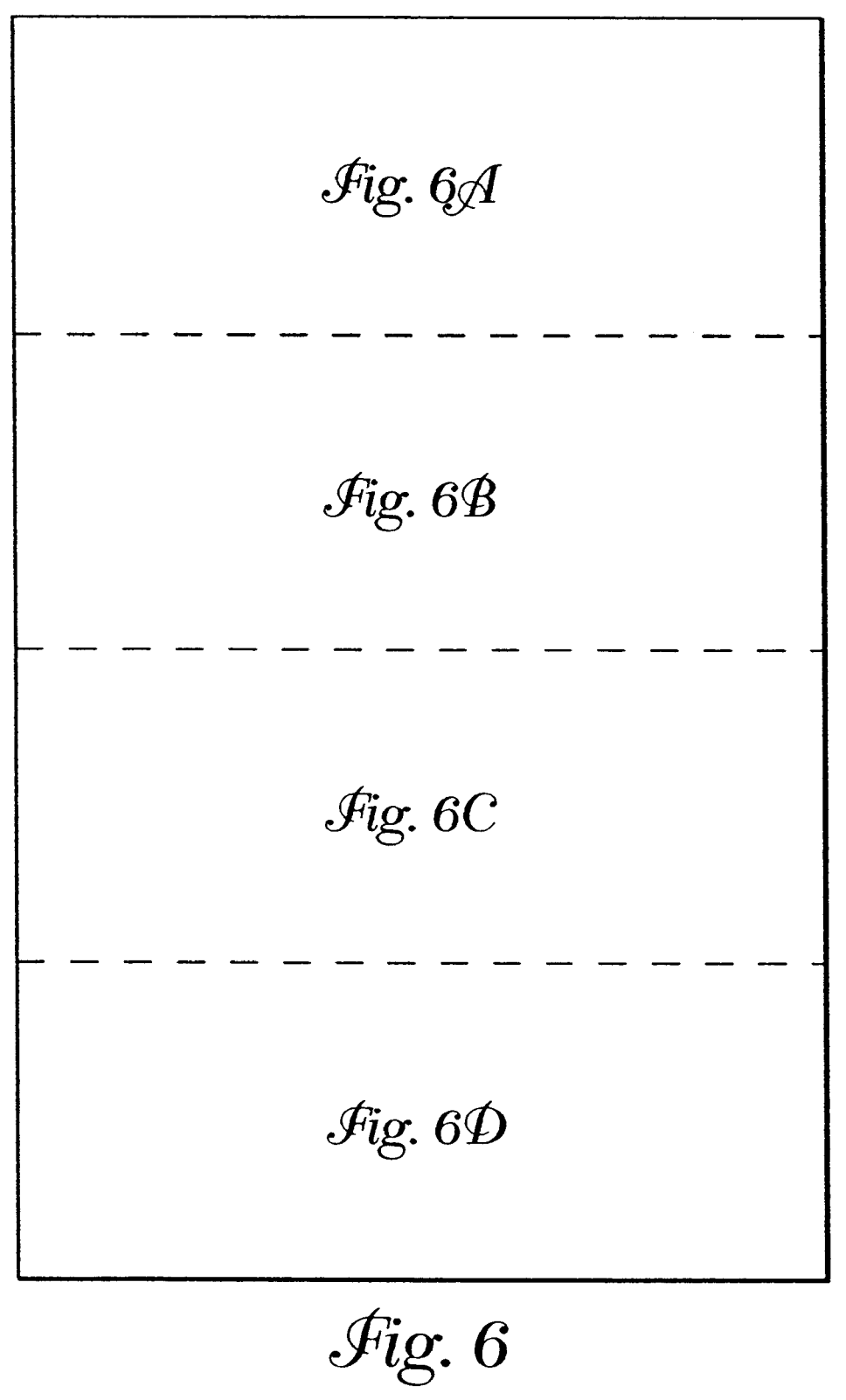

The DNA Sequence of the rodC gene from B. subtilis. Restriction sites are indicated. The translated protein sequence is also provided. This Figure also shows the mutation at position 1871, a "T for C" DNA substitution resulting in a "V for A" amino acid substitution. The DNA from this Sequence Chart 1 is listed as Sequence Identification number 1, SEQ. ID. NO. 1, (SEQ. ID. NO. 1 is the sequence without the mutation at position 1871). The protein from this FIG. 3 is listed in FIG. 4 and is listed as SEQ. ID. NO. 2. The numbers in the left margin in the Figure below indicate nucleic acid residues. The ATG shown below is the true start codon for the actual first amino acid of the isolated TAP enzyme. In practice, an upstream ribosome binding site is also required. The actual DNA sequence that was inserted into the plasmid is shown in FIG. 6. Here this protein, sequence shown below, SEQ. ID. 2, and FIG. 4, was actually expressed in E. coli using the plasmid pBSRODC1.

```
    ATGATTGAAAACACTGTGATT
  1 +---------+---------+
    M   I   E   N   T   V   I

AAATGTATTTTGAAAAGCTTGAAAAACAATTTAGGAAGTCTTGAATTGTTAATCTCAATT
 22 ---------+---------+---------+---------+---------+---------+
    K  C  I  L  K  S  L  K  N  N  L  G  S  L  E  L  L  I  S  I

GATTCAGAACACCAATTTTTAGAGGATTACCAGTTATTTTTAAAGCTGAAAGAGAGACGT
 82 ---------+---------+---------+---------+---------+---------+
    D  S  E  H  Q  F  L  E  D  Y  Q  L  F  L  K  L  K  E  R  R

TCAGGAACGGAATCTGAATTTCCGCTTCAAAACACTGGCTCATTAGAGTATAAAACTGAG
142 ---------+---------+---------+---------+---------+---------+
    S  G  T  E  S  E  F  P  L  Q  N  T  G  S  L  E  Y  K  T  E

ATAAATGCTCATGTTTTGCCTATGCCTGTTGAAATGGGACAAACATATGATTTTTATGTC
202 ---------+---------+---------+---------+---------+---------+
    I  N  A  H  V  L  P  M  P  V  E  M  G  Q  T  Y  D  F  Y  V

GAATTTCGAAAAAAATATGAAGATGCGGAGCAGGAACCACTCTTGAAGCGTCTTTCTGCT
```

```
                         -continued
    262 ---------+---------+---------+---------+---------+---------+
         E  F  R  K  K  Y  E  D  A  E  Q  E  P  L  L  K  R  L  S  A GAAGTAAATTCAATTGAGCGCGCCTTTCATGTCGATCAAACCACAGAACTTTTGATTTTA
    322 ---------+---------+---------+---------+---------+---------+
         E  V  N  S  I  E  R  A  F  H  V  D  Q  T  T  E  L  L  I  L CCTTATACAACTGATAAAGGCAACTTTTCTATTAAGGTGAAAAGAGAGGCCAAAATCATC
    382 ---------+---------+---------+---------+---------+---------+
         P  Y  T  T  D  K  G  N  F  S  I  K  V  K  R  E  A  K  I  I AGATTTGATCAAATCGAGATTAGCTCTGAAGAAATAAGCATAACAGGTTATGCGGGGTAC
    442 ---------+---------+---------+---------+---------+---------+
         R  F  D  Q  I  E  I  S  S  E  E  I  S  I  T  G  Y  A  G  Y CTGAGTTCCGAAAATCAATATCGGATAAAAAACTTGAACCTTATTTTAAAAAAGGGTGGA
    502 ---------+---------+---------+---------+---------+---------+
         L  S  S  E  N  Q  Y  R  I  K  N  L  N  L  I  L  K  K  G  G GAAACACCTATTGAGGAAAAATTTCCAATCAAGCTAGAAAGAAAAACACATGGCCTGGAA
    562 ---------+---------+---------+---------+---------+---------+
         E  T  P  I  E  E  K  F  P  I  K  L  E  R  K  T  H  G  L  E AACATGAGAGCAGATGGTTTTGTTCCGGAACTGTATGATTTTGAAGTGAAAGTGCCTTTG
    622 ---------+---------+---------+---------+---------+---------+
         N  M  R  A  D  G  F  V  P  E  L  Y  D  F  E  V  K  V  P  L AAAGAAATTCCTTTCTCAAATGAAAAACGTTATGTTTATCGTCTTTTTATGGAGTATATA
    682 ---------+---------+---------+---------+---------+---------+
         K  E  I  P  F  S  N  E  K  R  Y  V  Y  R  L  F  M  E  Y  I TGCAATGACGATGAAGGAACGGATATTCAGTTCAACAGCACTGCTCTTGTTTTAGGAGAT
    742 ---------+---------+---------+---------+---------+---------+
         C  N  D  D  E  G  T  D  I  Q  F  N  S  T  A  L  V  L  G  D CGAAAAAACAAATTAAAAGGATTAGTAAGTATTATTAAAACAAACAACGCACCAGTTCGT
    802 ---------+---------+---------+---------+---------+---------+
         R  K  N  K  L  K  G  L  V  S  I  I  K  T  N  N  A  P  V  R TATGAAGTCTTTAAGAAAAAGAAAAAGCAGACTCTAGGTATCAGAGTAAACGACTATAGC
    862 ---------+---------+---------+---------+---------+---------+
         Y  E  V  F  K  K  K  K  K  Q  T  L  G  I  R  V  N  D  Y  S CTGAAAACAAGGATGAAATACTTTATTAAAGGAAAGAAGAAGAGATTAGTATCAAAAATA
    922 ---------+---------+---------+---------+---------+---------+
         L  K  T  R  M  K  Y  F  I  K  G  K  K  K  R  L  V  S  K  I AAAAAGATCACAAAAATGAGAAACAAGTTAATCACTAAAACATACAAATCTCTATTCATG
    982 ---------+---------+---------+---------+---------+---------+
         K  K  I  T  K  M  R  N  K  L  I  T  K  T  Y  K  S  L  F  M ATGGCTAGCAGAATGCCAGTTAAAAGGAAAACAGTCATTTTTGAAAGTTTTAATGGGAAA
   1042 ---------+---------+---------+---------+---------+---------+
         M  A  S  R  M  P  V  K  R  K  T  V  I  F  E  S  F  N  G  K CAATACAGTTGTAATCCGAGAGCGATTTACGAATATATGCGGGAAAACCACCCTGAGTAT
   1102 ---------+---------+---------+---------+---------+---------+
         Q  Y  S  C  N  P  R  A  I  Y  E  Y  M  R  E  N  H  P  E  Y AAAATGTATTGGAGTGTAAATAAACAATATTCAGCGCCTTTTGATGAAAAGGGAATTCCT
   1162 ---------+---------+---------+---------+---------+---------+
         K  M  Y  W  S  V  N  K  Q  Y  S  A  P  F  D  E  K  G  I  P TACATTAATCGCCTCTCATTAAAATGGCTCTTCGCTATGGCAAGAGCTGAGTATTGGGTT
   1222 ---------+---------+---------+---------+---------+---------+
         Y  I  N  R  L  S  L  K  W  L  F  A  M  A  R  A  E  Y  W  V GTTAACAGCCGGCTTCCATTATGGATTCCGAAACCTAGTCATACAACATATTTACAAACA
   1282 ---------+---------+---------+---------+---------+---------+
         V  N  S  R  L  P  L  W  I  P  K  P  S  H  T  T  Y  L  Q  T TGGCATGGCACACCTTTAAAAAGACTTGCAATGGATATGGAAGAAGTCCATATGCCTGGT
   1342 ---------+---------+---------+---------+---------+---------+
         W  H  G  T  P  L  K  R  L  A  M  D  M  E  E  V  H  M  P  G ACAAACACCAAAAAATATAAAAGGAATTTATCAAGGAAGCTTCTAATTGGGATTACTTG
   1402 ---------+---------+---------+---------+---------+---------+
         T  N  T  K  K  Y  K  R  N  F  I  K  E  A  S  N  W  D  Y  L

ATTTCCCCAAATGGTTATTCAACTGAGATCTTTACACGGGCGTTTCAGTTTAACAAGACA
```

-continued

```
      ISPNGYSTEIFTRAFQFNKT

ATGATTGAATCTGGATATCCTAGAAATGATTTTCTTCATAATGATAATAATGAGGAAACA
1522  ---------+---------+---------+---------+---------+---------+
      M  I  E  S  G  Y  P  R  N  D  F  L  H  N  D  N  N  E  E  T

ATATCATTGATAAAGAGTAGGTTAAATATTCCTCGTGATAAAAAGGTTATTTTATATGCC
1582  ---------+---------+---------+---------+---------+---------+
      I  S  L  I  K  S  R  L  N  I  P  R  D  K  K  V  I  L  Y  A

CCTACATGGAGAGATGATCAGTTCTATGCAAAAGGGCGTTATAAGTTCGATCTCGATTTA
1642  ---------+---------+---------+---------+---------+---------+
      P  T  W  R  D  D  Q  F  Y  A  K  G  R  Y  K  F  D  L  D  L

GATTTGCATCAACTTAGACAAGAACTTGGAAATGAATATATTGTAATCTTAAGAATGCAT
1702  ---------+---------+---------+---------+---------+---------+
      D  L  H  Q  L  R  Q  E  L  G  N  E  Y  I  V  I  L  R  M  H

T
      TATCTGGTAGCTGAGAATTTTGATTTAGGTCCTTTTGAAGGATTTGCATATGATTTTTCT
1762  ---------+---------+---------+---------+---------+---------+
      Y  L  V  A  E  N  F  D  L  G  P  F  E  G  F  A  Y  D  F  S
            V

GCTTATGAGGATATTCGAGAATTGTATATGGTTTCTGATTTGCTGATTACTGATTATTCT
1822  ---------+---------+---------+---------+---------+---------+
      A  Y  E  D  I  R  E  L  Y  M  V  S  D  L  L  I  T  D  Y  S

TCAGTATTCTTTGATTTTGCAAATTTAAAACGGCCAATGCTATTCTTTGTCCCTGACATC
1882  ---------+---------+---------+---------+---------+---------+
      S  V  F  F  D  F  A  N  L  K  R  P  M  L  F  F  V  P  D  I

GAAACCTACCGGGACAAGTTGCGTGGTTTCTACTTTGATTTTGAAAAAGAAGCTCCTGGT
1942  ---------+---------+---------+---------+---------+---------+
      E  T  Y  R  D  K  L  R  G  F  Y  F  D  F  E  K  E  A  P  G

CCTTTGGTAAAAACTACTGAAGAAACGATTGAGGCTATCAAGCAGATCTCATCGCCTGAT
2002  ---------+---------+---------+---------+---------+---------+
      P  L  V  K  T  T  E  E  T  I  E  A  I  K  Q  I  S  S  P  D

TATAAGCTTCCGGTTTCTTTTGGTCCTTTCTATGATAAGTTTTGCTATTTAGAGTCAGGA
2064  ---------+---------+---------+---------+---------+---------+
      Y  K  L  P  V  S  F  G  P  F  Y  D  K  F  C  Y  L  E  S  G

CGTTCATCTGAAAAGGTTGTTAATACTGTATTTAAAGCTGAATAATTTAGGGGATCCAAAT
2122  ---------+---------+---------+---------+---------+---------+
      R  S  S  E  K  V  V  N  T  V  F  K  A  E  *
```

FIG. 4

Figure 4:
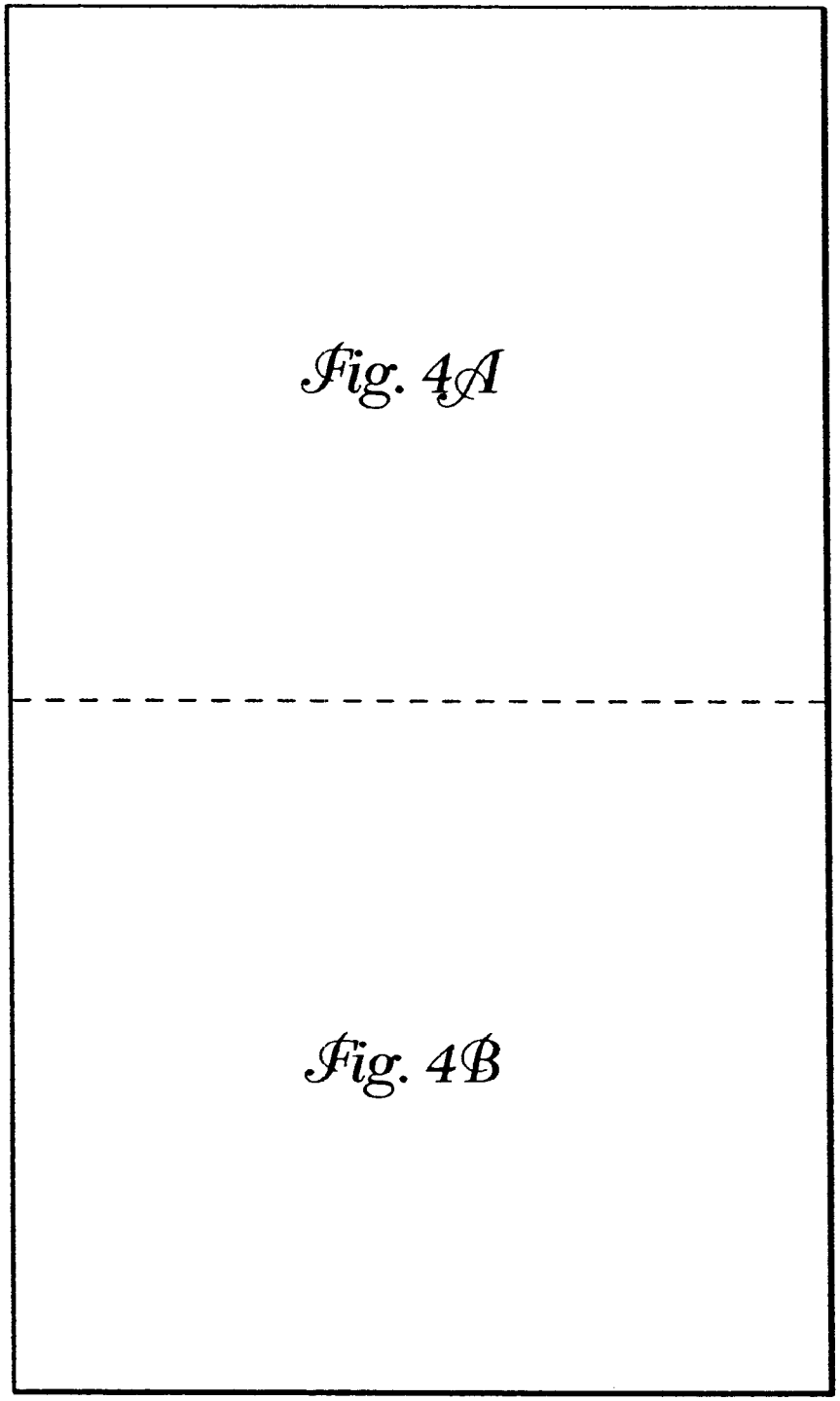
FIG. 4. The protein sequence for the TAP enzyme. These sequences are provided in SEQ. ID. No. 2. The amino acids, or protein from FIG. 3, including the single amino acid mutation are shown. The amino acids from this FIG. 4 are listed in as SEQuence IDentification Number 2 (SEQ. I.D. NO. 2 is the sequence without the mutation at position 616).

The amino acids, or protein from FIG. 3, including the single amino acid mutation, shown below. The amino acids from this FIG. 4 are listed in as SEQuence IDentification Number 2 (SEQ. I.D. NO. 2 is the sequence without the mutation at position 616).

```
  1   M I E N T V I
  8   K C I L K S L K N N L G S L E L L I S I
 28   D S E H Q F L E D Y Q L F L K L K E R R
 48   S G T E S E F P L Q N T G S L E Y K T E
 68   I N A H V L P M P V E M G Q T Y D F Y V
 88   E F R K K Y E D A E Q E P L L K R L S A
108   E V N S I E R A F H V D Q T T E L L I L
128   P Y T T D K G N F S I K V K R E A K I I
148   R F D Q I E I S S E E I S I T G Y A G Y
168   L S S E N Q Y R I K N L N L I L K K G G
188   E T P I E E K F P I K L E R K T H G L E
208   N M R A D G F V P E L Y D F E V K V P L
228   K E I P F S N E K R Y V Y R L F M E Y I
248   C N D D E G T D I Q F N S T A L V L G D
268   R K N K L K G L V S I I K T N N A P V R
288   Y E V F K K K K Q T L G I R V N D Y S
308   L K T R M K Y F I K G K K K R L V S K I
328   K K I T K M R N K L I T K T Y K S L F M
348   M A S R M P V K R K T V I F E S F N G K
368   Q Y S C N P R A I Y E Y M R E N H P E Y
388   K M Y W S V N K Q Y S A P F D E K G I P
408   Y I N R L S L K W L F A M A R A E Y W V
428   V N S R L P L W I P K P S H T T Y L Q T
```

-continued

```
448   W H G T P L K R L A M D M E E V H M P G
468   T N T K K Y K R N F I K E A S N W D Y L
488   I S P N G Y S T E I F T R A F Q F N K T
508   M I E S G Y P R N D F L H N D N N E E T
528   I S L I K S R L N I P R D K K V I L Y A
548   P T W R D D Q F Y A K G R Y K F D L D L
568   D L H Q L R Q E L G N E Y I V I L R M H
588   Y L V A E N F D L G P F E G F A Y D F S
                V
608   A Y E D I R E L Y M V S D L L I T D Y S
628   S V F F D F A N L K R P M L F F V P D I
648   E T Y R D K L R G F Y F D F E K E A P G
668   P L V K T T E E T I E A I K Q I S S P D
688   Y K L P V S F G P F Y D K F C Y L E S G
708   R S S E K V V N T V F K A E - 721
```

FIG. 5

The following two primers were used to clone rodC from *B. subtilits*.

C1A is 5'-TTCAGGATCCTTCTCTTGGAGGGTCACGGAAATAAAAG-3', this is sequence I.D. number 3.

And C2A is 5'-ATTTGGATCCCCTAAATTATTCAGCTTTAAATAC-3', this is sequence I.D. number 4.

FIG. 6

The DNA Sequence of the rodC gene from *B. subtilis*. Restriction sites are indicated. The putative translated protein sequence is also provided. This Figure also shows the mutation at position 1871, a "T for C" DNA substitution resulting in a "V for A" amino acid substitution. The DNA from this Sequence Figure is listed as Sequence Identification number 5 (seq. I.D. no.5 is the sequence without the mutation at position 1871). The protein only from this Sequence Figure is listed in FIG. 7 and is listed as SEQ. ID. NO. 6. The numbers in the left margin in the Figure below indicate nucleic acid residues. The ATG at nucleic acid residue 25–27 corresponds to the methionine translation start site predicted through computer analysis by reference to Honeyman and Stewart. The ATG underlined in nucleic acid residues 100–102 corresponds to the methionine (underlined and bold M) which is the actual first amino acid of the isolated TAP enzyme. Note, the actual DNA sequence, (with restriction sites noted), that was inserted into the plasmid is shown here and it includes an upstream ribosome binding site that is downstream from the putative start codon at position 25–27. The actual ribosome binding site is at position, 83–87. The actual ribosome binding site is apparently AGGAG, other ribosome binding sites could be engineered such as in AGGAGA site.

See SEQ. ID. NO.s 1 and 2

```
        BamHI
          |
     TTTTGGATCCAAGGAAGAGAGTTAATGTCCTTAGTAGTTGACACTAATAAAAGGAAGCAA
  1  ---------+---------+---------+---------+---------+---------+
                          M   S   L   V   V   D   T   N   K   R   K   Q

AAAGGAAAGAGCTTTTATACAGAGGAGCAGAAAAAAGTAATGATTGAAAACACTGTGATT
 61  ---------+---------+---------+---------+---------+---------+
      K   G   K   S   F   Y   T   E   E   Q   K   K   V   M   I   E   N   T   V   I

HindIII
                  |
     AAATGTATTTTGAAAAGCTTGAAAAACAATTTAGGAAGTCTTGAATTGTTAATCTCAATT
121  ---------+---------+---------+---------+---------+---------+
      K   C   I   L   K   S   L   K   N   N   L   G   S   L   E   L   L   I   S   I GATTCAGAACACCAATTTTTAGAGGATTACCAGTTATTTTTAAAGCTGAAAGAGAGACGT
181  ---------+---------+---------+---------+---------+---------+
       D   S   E   H   Q   F   L   E   D   Y   Q   L   F   L   K   L   K   E   R   R TCAGGAACGGAATCTGAATTTCCGCTTCAAAACACTGGCTCATTAGAGTATAAAACTGAG
241  ---------+---------+---------+---------+---------+---------+
      S   G   T   E   S   E   F   P   L   Q   N   T   G   S   L   E   Y   K   T   E ATAAATGCTCATGTTTTGCCTATGCCTGTTGAAATGGGACAAACATATGATTTTTATGTC
301  ---------+---------+---------+---------+---------+---------+
      X   N   A   H   V   L   P   M   P   V   E   M   G   Q   T   Y   D   F   Y   V GAATTTCGAAAAAAATATGAAGATGCGGAGCAGGAACCACTCTTGAAGCGTCTTTCTGCT
361  ---------+---------+---------+---------+---------+---------+
      E   F   R   K   K   Y   E   D   A   E   Q   E   P   L   L   K   R   L   S   A GAAGTAAATTCAATTGAGCGCGCCTTTCATGTCGATCAAACCACAGAACTTTTGATTTTA
421  ---------+---------+---------+---------+---------+---------+
      E   V   N   S   I   E   R   A   F   H   V   D   Q   T   T   E   L   L   I   L CCTTATACAACTGATAAAGGCAACTTTTCTATTAAGGTGAAAAGAGAGGCCAAAATCATC
481  ---------+---------+---------+---------+---------+---------+
      P   Y   T   T   D   K   G   N   F   S   I   K   V   K   R   E   A   K   I   I
```

-continued

```
                                                                   KpnI
                                                                   |
     AGATTTGATCAAATCGAGATTAGCTCTGAAGAAATAAGCATAACAGGTTATGCGGGGTAC
 541 ---------+---------+---------+---------+---------+---------+
      R  F  D  Q  I  E  I  S  S  E  E  I  S  I  T  G  Y  A  G  Y

CTGAGTTCCGAAAATCAATATCGGATAAAAAACTTGAACCTTATTTTAAAAAGGGTGGA
 601 ---------+---------+---------+---------+---------+---------+
      L  S  S  E  N  Q  Y  R  I  K  N  L  N  L  I  L  K  K  G  G

GAAACACCTATTGAGGAAAAATTTCCAATCAAGCTAGAAAGAAAAACACATGGCCTGGAA
 661 ---------+---------+---------+---------+---------+---------+
      E  T  P  I  E  E  K  F  P  I  K  L  E  R  K  T  H  G  L  E

AACATGAGAGCAGATGGTTTTGTTCCGGAACTGTATGATTTTGAAGTGAAAGTGCCTTTG
 721 ---------+---------+---------+---------+---------+---------+
      N  M  R  A  D  G  F  V  P  E  L  Y  D  F  E  V  K  V  P  L

AAAGAAATTCCTTTCTCAAATGAAAAACGTTATGTTTATCGTCTTTTTATGGAGTATATA
 781 ---------+---------+---------+---------+---------+---------+
      K  E  I  P  F  S  N  E  K  R  Y  V  Y  R  L  F  M  E  Y  I

TGCAATGACGATGAAGGAACGGATATTCAGTTCAACAGCACTGCTCTTGTTTTAGGAGAT
 841 ---------+---------+---------+---------+---------+---------+
      C  N  D  D  E  G  T  D  I  Q  F  N  S  T  A  L  V  L  G  D

CGAAAAAACAAATTAAAAGGATTAGTAAGTATTATTAAAACAAACAACGCACCAGTTCGT
 901 ---------+---------+---------+---------+---------+---------+
      R  K  N  K  L  K  G  L  V  S  I  I  K  T  N  N  A  P  V  R

TATGAAGTCTTTAAGAAAAAGAAAAAGCAGACTCTAGGTATCAGAGTAAACGACTATAGC
 961 ---------+---------+---------+---------+---------+---------+
      Y  E  V  F  K  K  K  K  K  Q  T  L  G  I  R  V  N  D  Y  S

CTGAAAACAAGGATGAAATACTTTATTAAAGGAAAGAAGAAGAGATTAGTATCAAAAATA
1021 ---------+---------+---------+---------+---------+---------+
      L  K  T  R  M  K  Y  F  I  K  G  K  K  K  R  L  V  S  K  I

AAAAAGATCACAAAAATGAGAAACAAGTTAATCACTAAAACATACAAATCTCTATTCATG
1081 ---------+---------+---------+---------+---------+---------+
      K  K  I  T  K  M  R  N  K  L  I  T  K  T  Y  K  S  L  F  M

ATGGCTAGCAGAATGCCAGTTAAAAGGAAAACAGTCATTTTTGAAAGTTTTAATGGGAAA
1141 ---------+---------+---------+---------+---------+---------+
      M  A  S  R  M  P  V  K  R  K  T  V  I  F  E  S  F  N  G  K

CAATACAGTTGTAATCCGAGAGCGATTTACGAATATATGCGGGAAAACCACCCTGAGTAT
1201 ---------+---------+---------+---------+---------+---------+
      Q  Y  S  C  N  P  R  A  I  Y  E  Y  M  R  E  N  H  P  E  Y

EcoRI
                                                             |
     AAAATGTATTGGAGTGTAAATAAACAATATTCAGCGCCTTTTGATGAAAAGGGAATTCCT
1261 ---------+---------+---------+---------+---------+---------+
      K  M  Y  W  S  V  N  K  Q  Y  S  A  P  F  D  E  K  G  I  P

TACATTAATCGCCTCTCATTAAAATGGCTCTTCGCTATGGCAAGAGCTGAGTATTGGGTT
1321 ---------+---------+---------+---------+---------+---------+
      Y  I  N  R  L  S  L  K  W  L  F  A  M  A  R  A  E  Y  W  V

GTTAACAGCCGGCTTCCATTATGGATTCCGAAACCTAGTCATACAACATATTTACAAACA
1381 ---------+---------+---------+---------+---------+---------+
      V  N  S  R  L  P  L  W  I  P  K  P  S  H  T  T  Y  L  Q  T

TGGCATGGCACACCTTTAAAAAGACTTGCAATGGATATGGAAGAAGTCCATATGCCTGGT
1441 ---------+---------+---------+---------+---------+---------+
      W  H  G  T  P  L  K  R  L  A  M  D  M  E  E  V  H  M  P  G

HindIII
                                            |
     ACAAACACCAAAAAATATAAAAGGAATTTTATCAAGGAAGCTTCTAATTGGGATTACTTG
1501 ---------+---------+---------+---------+---------+---------+
      T  N  T  K  K  Y  K  R  N  F  I  K  E  A  S  N  W  D  Y  L ATTTCCCCAAATGGTTATTCAACTGAGATCTTTACACGGGCGTTTCAGTTTAACAAGACA
1561 ---------+---------+---------+---------+---------+---------+
      I  S  P  N  G  Y  S  T  E  I  F  T  R  A  F  Q  F  N  K  T ATGATTGAATCTGGATATCCTAGAAATGATTTTCTTCATAATGATAATAATGAGGAAACA
1621 ---------+---------+---------+---------+---------+---------+
```

```
                    M  I  E  S  G  Y  P  R  N  D  F  L  H  N  D  N  N  E  E  T

ATATCATTGATAAAGAGTAGGTTAAATATTCCTCGTGATAAAAAGGTTATTTTATATGCC
1681 ---------+---------+---------+---------+---------+---------+
     I  S  L  I  K  S  R  L  N  I  P  R  D  K  K  V  I  L  Y  A

CCTACATGGAGAGATGATCAGTTCTATGCAAAAGGGCGTTATAAGTTCGATCTCGATTTA
1741 ---------+---------+---------+---------+---------+---------+
     P  T  W  R  D  D  Q  F  Y  A  K  G  R  Y  K  F  D  L  D  L

GATTTGCATCAACTTAGACAAGAACTTGGAAATGAATATATTGTAATCTTAAGAATGCAT
1801 ---------+---------+---------+---------+---------+---------+
     D  L  H  Q  L  R  Q  E  L  G  N  E  Y  I  V  I  L  R  M  H

T
     TATCTGGTAGCTGAGAATTTTGATTTAGGTCCTTTTGAAGGATTTGCATATGATTTTTCT
1861 ---------+---------+---------+---------+---------+---------+
     Y  L  V  A  E  E  F  D  L  G  P  F  E  G  F  A  Y  D  F  S
              V

GCTTATGAGGATATTCGAGAATTGTATATGGTTTCTGATTTGCTGATTACTGATTATTCT
1921 ---------+---------+---------+---------+---------+---------+
     A  Y  E  D  I  R  E  L  Y  M  V  S  D  L  L  I  T  D  Y  S

TCAGTATTCTTTGATTTTGCAAATTTAAAACGGCCAATGCTATTCTTTGTCCCTGACATC
1981 ---------+---------+---------+---------+---------+---------+
     S  V  F  F  D  F  A  N  L  K  R  P  M  L  F  F  V  P  D  I

GAAACCTACCGGGACAAGTTGCGTGGTTTCTACTTTGATTTTGAAAAAGAAGCTCCTGGT
2041 ---------+---------+---------+---------+---------+---------+
     E  T  Y  R  D  K  L  R  G  F  Y  F  D  F  E  K  E  A  P  G

CCTTTTGGTAAAAACTACTGAAGAAACGATTGAGGCTATCAAGCAGATCTCATCGCCTGAT
2101 ---------+---------+---------+---------+---------+---------+
     P  L  V  K  T  T  E  E  T  I  E  A  I  K  Q  I  S  S  P  D

HindIII
           |
     TATAAGCTTCCGGTTTCTTTTGGTCCTTTCTATGATAAGTTTTGCTATTTAGAGTCAGGA
2161 ---------+---------+---------+---------+---------+---------+
     Y  K  L  P  V  S  F  G  P  F  Y  D  K  F  C  Y  L  E  S  G BamHI
                                                     |
     CGTTCATCTGAAAAGGTTGTTAATACTGTATTTAAAGCTGAATAATTTAGGGGATCCAAAT
2221 ---------+---------+---------+---------+---------+---------+
     R  S  S  E  K  V  V  N  T  V  F  K  A  E  *
```

FIG. 7

Figures 7, 7A, 7B:
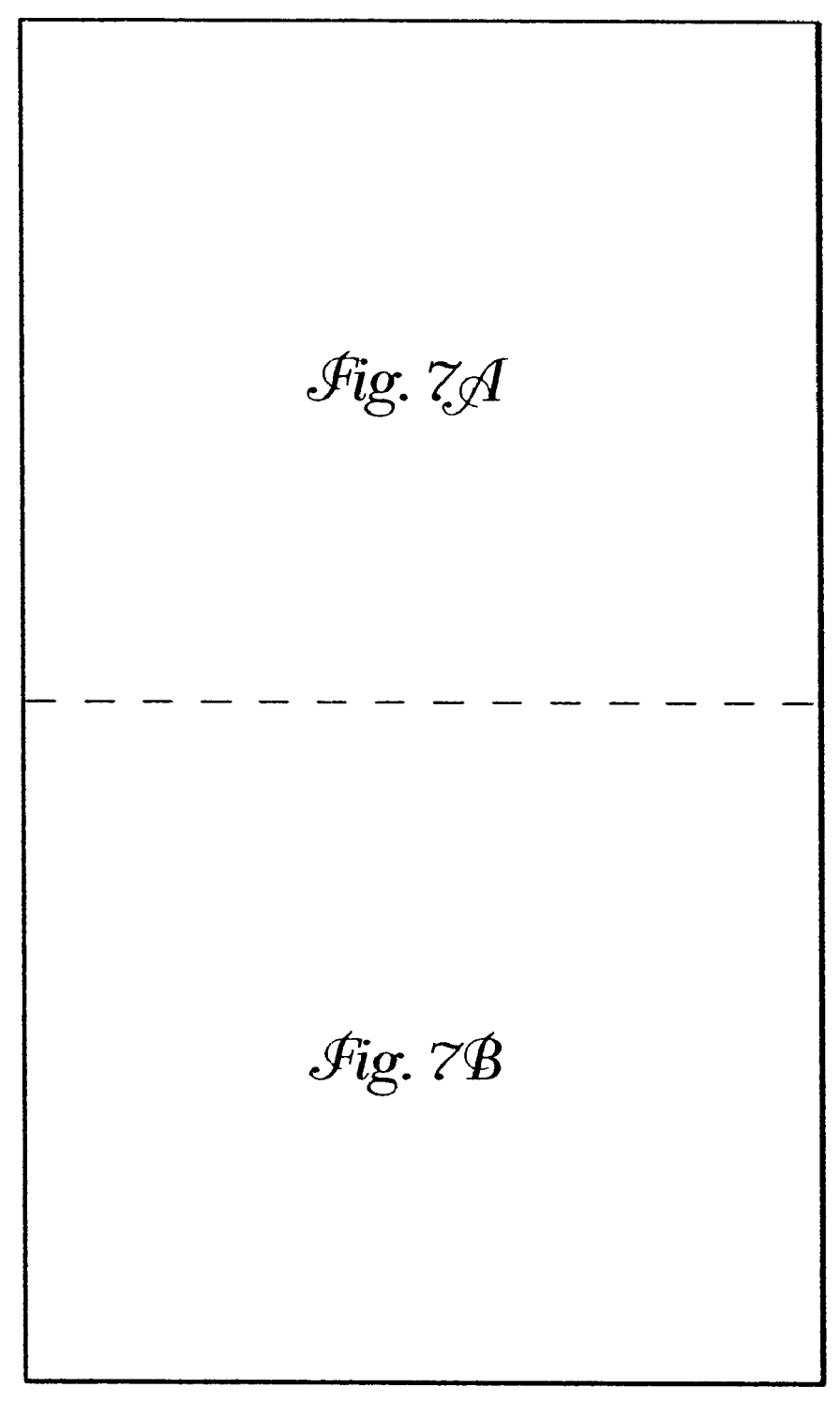

The putative amino acids, or protein from FIG. 6, including the single amino acid mutation, shown below. The amino acids from this FIG. 7 are listed separately as SEQ. ID. NO. 6 (SEQ. ID. NO. 6 is the sequence without the mutation at position 616).

```
  1    M S L V V D T N K R K Q

13    K G K S F Y T E E Q K K V M I E N T V I

33    K C I L K S L K N N L G S L E L L I S I

53    D S E H Q F L E D Y Q L F L K L K E R R

73    S G T E S E F P L Q N T G S L E Y K T E

93    I N A H V L P M P V E M G Q T Y D F Y V

113    E F R K K Y E D A E Q E P L L K R L S A

133    E V N S I E R A F H V D Q T T E L L I L

153    P Y T T D K G N F S I K V K R E A K I I

173    R F D Q I E I S S E E I S I T G Y A G Y

193    L S S E N Q Y R I K N L N L I L K K G G

213    E T P I E E K F P I K L E R K T H G L E

233    N M R A D G F V P E L Y D F E V K V P L

253    K E I P F S N E K R Y V Y R L F M E Y I

273    C N D D E G T D I Q F N S T A L V L G D

293    R K N K L K G L V S I I K T N N A P V R

313    Y E V F K K K K Q T L G I R V N D Y S

333    L K T R M K Y F I K G K K K R L V S K I

353    K K I T K M R N K L I T K T Y K S L F M

373    M A S R M P V K R K T V I F E S F N G K

393    Q Y S C N P R A I Y E Y M R E N H P E Y

413    K M Y W S V N K Q Y S A P F D E K G I P

433    Y I N R L S L K W L F A M A R A E Y W V

453    V N S R L P L W I P K P S H T T Y L Q T
```

```
473  W H G T P L K R L A M D M E E V H M P G

493  T N T K K Y K R N F I K E A S N W D Y L

513  I S P N G Y S T E I F T R A F Q F N K T

533  M I E S G Y P R N D F L H N D N N E E T

553  I S L I K S R L N I P R D K K V I L Y A

573  P T W R D D Q F Y A K G R Y K F D L D L

593  D L H Q L R Q E L G N E Y I V I L R M H
```

```
613  Y L V A E N F D L G P F E G F A Y D F S
                                           V

633  A Y E D I R E L Y M V S D L L I T D Y S

653  S V F F D A N L K R P M L F F V P D I

673  E T Y R D K L R G F Y D F E K E A P G

693  P L V K T T E E T I E A I K Q I S S P D

713  Y K L P V S F G P F Y D K F C Y L E S G

733  R S S E K V V N T V F K A E - 746
```

What is claimed is:

1. A process for determining teichoic acid polymerase activity in a sample, the method comprising:
combining CDP-glycerol, water, a lipoteichoic acid substrate from a bacterium selected from the group consisting of *Staphylococcus aureus, Enterococcus faecalis,* and *Bacillus subtilis,* and the sample to form a mixture;
incubating the mixture under conditions effective for a teichoic acid polymerase in the sample, to cause the incorporation of at least one glycerol-3-phosphate moiety into the lipoteichoic acid substrate to form a lipoteichoic acid product having at least one additional glycerol-3-phosphate moiety incorporated therein, wherein the teichoic acid polymerase is encoded by DNA having at least about 70% homology with SEQ ID NO:1; and
determining the presence or absence of the lipoteichoic acid product.

2. The process of claim 1 wherein determining the presence or absence of the lipoteichoic acid product comprises measuring the amount of the lipoteichoic acid product formed.

3. The process of claim 1 wherein determining the presence or absence of the lipoteichoic acid product comprises adding an acid to the mixture after incubation to precipitate the lipoteichoic acid product.

4. The process of claim 1 wherein the CDP-glycerol is CDP[$^3$H]glycerol.

5. The process of claim 4 wherein determining the presence or absence of the lipoteichoic acid product comprises:
adding streptavidin SPA beads comprising a lectin to the mixture after incubation to bind the lipoteichoic acid product; and
measuring the amount of lipoteichoic acid product bound to the SPA beads.

6. The process of claim 1 wherein the teichoic acid polymerase comprises SEQ ID No: 2.

7. The process of claim 1 wherein the teichoic acid polymerase comprises the first 20 N-terminal amino residues of SEQ ID No: 2.

8. The process of claim 1 wherein the lipoteichoic acid substrate is pretreated to remove alanine bound to the lipoteichoic acid as an ester and free alanine associated with lipoteichoic acid in solution before the lipoteichoic acid substrate is combined with the other ingredients.

9. A process for determining the presence or absence of lipoteichoic acid from a bacterium selected from the group consisting of *Staphylococcus aureus, Enterococcus faecalis,* and *Bacillus subtilis* in a sample, the method comprising:
combining CDP-glycerol, water, a teichoic acid polymerase encoded by DNA having at least about 70% homology with SEQ ID NO:1, and the sample to form a mixture;
incubating the mixture under conditions effective for the teichoic acid polymerase to cause the incorporation of at least one glycerol-3-phosphate moiety into a lipoteichoic acid present in the sample to form a lipoteichoic acid product having at least one additional glycerol-3-phosphate moiety incorporated therein; and
determining the presence or absence of the lipoteichoic acid product.

10. The process of claim 9 wherein determining the presence or absence of the lipoteichoic acid product comprises measuring the amount of the lipoteichoic acid product formed.

11. The process of claim 9 wherein determining the presence or absence of the lipoteichoic acid product comprises adding an acid to the mixture after incubation to precipitate the lipoteichoic acid product.

12. The process of claim 9 wherein the CDP-glycerol is CDP[$^3$H]glycerol.

13. The process of claim 12 wherein determining the presence or absence of the lipoteichoic acid product comprises:
adding streptavidin SPA beads comprising a lectin to the mixture after incubation to bind the lipoteichoic acid product; and
measuring the amount of lipoteichoic acid product bound to the SPA beads.

14. The process of claim 9 wherein the teichoic acid polymerase is expressed from a cloned cell.

15. The process of claim 14 wherein the teichoic acid polymerase comprises the first 20 N-terminal amino residues of SEQ ID No: 2.

16. The process of claim 9 wherein the teichoic acid polymerase is a soluble enzyme.

17. A process for screening teichoic acid polymerase inhibitors, the method comprising:
combining CDP-glycerol, water, a lipoteichoic acid substrate from a bacterium selected from the group consisting of *Staphylococcus aureus, Enterococcus faecalis,* and *Bacillus subtilis,* a teichoic acid polymerase encoded by DNA having at least about 70% homology with SEQ ID NO:1, and a teichoic acid polymerase inhibitor to form a mixture;

incubating the mixture under conditions effective, when the teichoic acid polymerase inhibitor is not present, for the teichoic acid polymerase to cause the incorporation of at least one glycerol-3-phosphate moiety into the lipoteichoic acid substrate to form a lipoteichoic acid product having at least one additional glycerol-3-phosphate moiety incorporated therein; and determining the presence or absence of the lipoteichoic acid product produced when the teichoic acid polymerase inhibitor is present in the mixture relative to the lipoteichoic acid product produced when the teichoic acid polymerase inhibitor is not present in the mixture.

18. The process of claim 17 wherein determining the presence or absence of the lipoteichoic acid product comprises measuring the amount of the lipoteichoic acid product formed.

19. The process of claim 17 wherein determining the presence or absence of the lipoteichoic acid product comprises adding an acid to the mixture after incubation to precipitate the lipoteichoic acid product.

20. The process of claim 17 wherein the CDP-glycerol is CDP[$^3$H]glycerol.

21. The process of claim 20 wherein determining the presence or absence of the lipoteichoic acid product comprises:

adding streptavidin SPA beads comprising a lectin to the mixture after incubation to bind the lipoteichoic acid product; and measuring the amount of lipoteichoic acid product bound to the SPA beads.

22. A process for monitoring enzymatic reactions catalyzed by teichoic acid polymerase, the method comprising:

combining CDP-glycerol, water, a lipoteichoic acid substrate from a bacterium selected from the group consisting of *Staphylococcus aureus, Enterococcus faecalis,* and *Bacillus subtilis,* and a teichoic acid polymerase encoded by DNA having at least about 70% homology with SEQ ID NO:1, to form a mixture;

incubating the mixture under conditions effective for the teichoic acid polymerase to cause the incorporation of at least one glycerol-3-phosphate moiety into the lipoteichoic acid substrate to form a lipoteichoic acid product having at least one additional glycerol-3-phosphate moiety incorporated therein; and determining the presence or absence of the lipoteichoic acid product.

23. The process of claim 22 wherein determining the presence or absence of the lipoteichoic acid product comprises measuring the amount of the lipoteichoic acid product formed.

24. The process of claim 22 wherein determining the presence or absence of the lipoteichoic acid product comprises adding an acid to the mixture after incubation to precipitate the lipoteichoic acid product.

25. The process of claim 22 wherein the CDP-glycerol is CDP[$^3$H]glycerol.

26. The process of claim 25 wherein determining the presence or absence of the lipoteichoic acid product comprises:

adding streptavidin SPA beads comprising a lectin to the mixture after incubation to bind the lipoteichoic acid product; and measuring the amount of lipoteichoic acid product bound to the SPA beads.

27. The process of claim 1 wherein the teichoic acid polymerase is encoded by DNA represented by SEQ ID NO:1.

28. The process of claim 1 wherein the amino acid sequence of the teichoic acid polymerase has at least about 70% homology with SEQ ID NO:2.

29. The process of claim 1 wherein the amino acid sequence of the teichoic acid polymerase comprises an amino acid sequence represented by SEQ ID NO:2.

30. The process of claim 9 wherein the teichoic acid polymerase is encoded by DNA represented by SEQ ID NO:1.

31. The process of claim 9 wherein the amino acid sequence of the teichoic acid polymerase has at least about 70% homology with SEQ ID NO:2.

32. The process of claim 9 wherein the amino acid sequence of the teichoic acid polymerase comprises an amino acid sequence represented by SEQ ID NO:2.

33. The process of claim 17 wherein the teichoic acid polymerase is encoded by DNA represented by SEQ ID NO:1.

34. The process of claim 17 wherein the amino acid sequence of the teichoic acid polymerase has at least about 70% homology with SEQ ID NO:2.

35. The process of claim 17 wherein the amino acid sequence of the teichoic acid polymerase comprises an amino acid sequence represented by SEQ ID NO:2.

36. The process of claim 22 wherein the teichoic acid polymerase is encoded by DNA represented by SEQ ID NO:1.

37. The process of claim 22 wherein the amino acid sequence of the teichoic acid polymerase has at least about 70% homology with SEQ ID NO:2.

38. The process of claim 22 wherein the amino acid sequence of the teichoic acid polymerase comprises an amino acid sequence represented by SEQ ID NO:2.

39. A process for determining teichoic acid polymerase activity in a sample, the method comprising:

combining CDP-glycerol, water, a lipoteichoic acid substrate from a bacterium selected from the group consisting of *Staphylococcus aureus, Enterococcus faecalis,* and *Bacillus subtilis,* and the sample to form a mixture;

incubating the mixture under conditions effective for a teichoic acid polymerase in the sample to cause the incorporation of at least one glycerol-3-phosphate moiety into the lipoteichoic acid substrate to form a lipoteichoic acid product having at least one additional glycerol-3-phosphate moiety incorporated therein, wherein the teichoic acid polymerase has an amino acid sequence with at least about 70% homology with SEQ ID NO:2; and determining the presence or absence of the lipoteichoic acid product.

40. The process of claim 39 wherein determining the presence or absence of the lipoteichoic acid product comprises measuring the amount of the lipoteichoic acid product formed.

41. The process of claim 39 wherein determining the presence or absence of the lipoteichoic acid product comprises adding an acid to the mixture after incubation to precipitate the lipoteichoic acid product.

42. The process of claim 39 wherein the CDP-glycerol is CDP[$^3$H]glycerol and wherein determining the presence or absence of the lipoteichoic acid product comprises:

adding streptavidin SPA beads comprising a lectin to the mixture after incubation to bind the lipoteichoic acid product; and measuring the amount of lipoteichoic acid product bound to the SPA beads.

43. A process for determining the presence or absence of lipoteichoic acid from a bacterium selected from the group consisting of *Staphylococcus aureus, Enterococcus faecalis,* and *Bacillus subtilis* in a sample, the method comprising:

combining CDP-glycerol, water, a teichoic acid polymerase having an amino acid sequence with at least about 70% homology with SEQ ID NO:2, and the sample to form a mixture;

incubating the mixture under conditions effective for the teichoic acid polymerase to cause the incorporation of at least one glycerol-3-phosphate moiety into a lipoteichoic acid present in the sample to form a lipoteichoic acid product having at least one additional glycerol-3-phosphate moiety incorporated therein; and determining the presence or absence of the lipoteichoic acid product.

44. The process of claim 43 wherein determining the presence or absence of the lipoteichoic acid product comprises measuring the amount of the lipoteichoic acid product formed.

45. The process of claim 43 wherein determining the presence or absence of the lipoteichoic acid product comprises adding an acid to the mixture after incubation to precipitate the lipoteichoic acid product.

46. The process of claim 43 wherein the CDP-glycerol is CDP[$^3$H]glycerol and wherein determining the presence or absence of the lipoteichoic acid product comprises:

adding streptavidin SPA beads comprising a lectin to the mixture after incubation to bind the lipoteichoic acid product; and measuring the amount of lipoteichoic acid product bound to the SPA beads.

47. A process for screening teichoic acid polymerase inhibitors, the method comprising:

combining CDP-glycerol, water, a lipoteichoic acid substrate from a bacterium selected from the group consisting of *Staphylococcus aureus, Enterococcus faecalis,* and *Bacillus subtilis,* a teichoic acid polymerase having an amino acid sequence with at least about 70% homology with SEQ ID NO:2, and a teichoic acid polymerase inhibitor to form a mixture;

incubating the mixture under conditions effective, when the teichoic acid polymerase inhibitor is not present, for the teichoic acid polymerase to cause the incorporation of at least one glycerol-3-phosphate moiety into the lipoteichoic acid substrate to form a lipoteichoic acid product having at least one additional glycerol-3-phosphate moiety incorporated therein; and determining the presence or absence of the lipoteichoic acid product produced when the teichoic acid polymerase inhibitor is present in the mixture relative to the lipoteichoic acid product produced when the teichoic acid polymerase inhibitor is not present in the mixture.

48. The process of claim 47 wherein determining the presence or absence of the lipoteichoic acid product comprises measuring the amount of the lipoteichoic acid product formed.

49. The process of claim 47 wherein determining the presence or absence of the lipoteichoic acid product comprises adding an acid to the mixture after incubation to precipitate the lipoteichoic acid product.

50. The process of claim 47 wherein the CDP-glycerol is CDP[$^3$H]glycerol and wherein determining the presence or absence of the lipoteichoic acid product comprises:

adding streptavidin SPA beads comprising a lectin to the mixture after incubation to bind the lipoteichoic acid product; and measuring the amount of lipoteichoic acid product bound to the SPA beads.

51. A process for monitoring enzymatic reactions catalyzed by teichoic acid polymerase, the method comprising:

combining CDP-glycerol, water, a lipoteichoic acid substrate from a bacterium selected from the group consisting of *Staphylococcus aureus, Enterococcus faecalis,* and *Bacillus subtilis,* and a teichoic acid polymerase having an amino acid sequence with at least about 70% homology with SEQ ID NO:2 to form a mixture;

incubating the mixture under conditions effective for the teichoic acid polymerase to cause the incorporation of at least one glycerol-3-phosphate moiety into the lipoteichoic acid substrate to form a lipoteichoic acid product having at least one additional glycerol-3-phosphate moiety incorporated therein; and determining the presence or absence of the lipoteichoic acid product.

52. The process of claim 51 wherein determining the presence or absence of the lipoteichoic acid product comprises measuring the amount of the lipoteichoic acid product formed.

53. The process of claim 51 wherein determining the presence or absence of the lipoteichoic acid product comprises adding an acid to the mixture after incubation to precipitate the lipoteichoic acid product.

54. The process of claim 51 wherein the CDP-glycerol is CDP[$^3$H]glycerol and wherein determining the presence or absence of the lipoteichoic acid product comprises:

adding streptavidin SPA beads comprising a lectin to the mixture after incubation to bind the lipoteichoic acid product; and measuring the amount of lipoteichoic acid product bound to the SPA beads.

* * * * *